（12） United States Patent
Palecek et al.

(10) Patent No.: US 9,290,741 B2
(45) Date of Patent: Mar. 22, 2016

(54) SIMPLIFIED METHODS FOR GENERATING ENDOTHELIAL CELLS FROM HUMAN PLURIPOTENT STEM CELLS UNDER DEFINED CONDITIONS

(71) Applicant: Wisconsin Alumni Research Foundation, Madison, WI (US)

(72) Inventors: Sean Paul Palecek, Verona, WI (US); Xiaojun Lian, Dongtai (CN); Xiaoping Bao, Dongtai (CN)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 14/212,125

(22) Filed: Mar. 14, 2014

(65) Prior Publication Data
US 2014/0287498 A1 Sep. 25, 2014

Related U.S. Application Data

(60) Provisional application No. 61/792,589, filed on Mar. 15, 2013.

(51) Int. Cl.
*C12N 5/00* (2006.01)
*C12N 5/071* (2010.01)

(52) U.S. Cl.
CPC .......... *C12N 5/069* (2013.01); *C12N 2501/415* (2013.01); *C12N 2506/02* (2013.01)

(58) Field of Classification Search
CPC ............... C12N 5/069; C12N 2501/40; C12N 2501/405
USPC .......................................... 435/325, 366, 375
See application file for complete search history.

(56) References Cited

U.S. PATENT DOCUMENTS

2010/0221833 A1* 9/2010 Chung et al. ................. 435/377

OTHER PUBLICATIONS

Bakre et al. J Biol Chem 2007;282:31703-12.*
An et al. NCBI Bookshelf 2012.*
Baba, Yoshihiro, Karla P. Garrett, and Paul W. Kincade. "Constitutively active β-catenin confers multilineage differentiation potential on lymphoid and myeloid progenitors," Immunity 23.6 (2005): 599-609.
Grigoriadis, Agamemnon E., et al. "Directed differentiation of hematopoietic precursors and functional osteoclasts from human ES and iPS cells." Blood 115.14 (2010): 2769-2776.
Hagen, Thilo, et al. "Expression and characterization of GSK-3 mutants and their effect on β-catenin phosphorylation in intact cells." Journal of Biological Chemistry 277.26 (2002): 23330-23335.
Kattman, Steven J., et al. "Stage-specific optimization of activin/nodal and BMP signaling promotes cardiac differentiation of mouse and human pluripotent stem cell lines." Cell stem cell 8.2 (2011): 228-240.
Laflamme, Michael A., et al. "Cardiomyocytes derived from human embryonic stem cells in pro-survival factors enhance function of infarcted rat hearts." Nature biotechnology 25.9 (2007): 1015-1024.
Lian, Xiaojun, et al. "Robust cardiomyocyte differentiation from human pluripotent stem cells via temporal modulation of canonical Wnt signaling." Proceedings of the National Academy of Sciences 109.27 (2012): E1848-E1857.
Lian, Xiaojun, et al. "Insulin inhibits cardiac mesoderm, not mesendoderm, formation during cardiac differentiation of human pluripotent stem cells and modulation of canonical Wnt signaling can rescue this inhibition." Stem Cells 31.3 (2013): 447-457.
Lian, Xiaojun, et al. "Directed cardiomyocyte differentiation from human pluripotent stem cells by modulating Wnt/β-catenin signaling under fully defined conditions." Nature protocols 8.1 (2013): 162-175.
Paige, Sharon L., et al. "Endogenous Wnt/β-catenin signaling is required for cardiac differentiation in human embryonic stem cells." PLoS One 5.6 (2010): e11134.
Tatsumi, Rie, et al. "Simple and highly efficient method for production of endothelial cells from human embryonic stem cells." Cell transplantation 20.9 (2011): 1423-1430.
Tran, Thanh H., et al. "Wnt3a—Induced Mesoderm Formation and Cardiomyogenesis in Human Embryonic Stem Cells." Stem Cells 27.8 (2009): 1869-1878.
Wong, Wing Tak, et al. "Endothelial cells derived from nuclear reprogramming." Circulation research 111.10 (2012): 1363-1375.
Yu, Pengzhi, et al. "FGF2 sustains NANOG and switches the outcome of BMP4-induced human embryonic stem cell differentiation." Cell stem cell 8.3 (2011): 326-334.
Zhang, Q., Jiang, J., Han, P., Yuan, Q., Zhang, J., Zhang, X., . . . & Ma, Y. (2011). Direct differentiation of atrial and ventricular myocytes from human embryonic stem cells by alternating retinoid signals. Cell research, 21(4), 579-587.

* cited by examiner

*Primary Examiner* — Janice Li
(74) *Attorney, Agent, or Firm* — Quarles & Brady LLP

(57) ABSTRACT

Methods for generating human endothelial cells from human pluripotent stem cells under defined conditions in the absence of VEGF are described. Wnt/β-catenin signaling is activated in human pluripotent stem cells for a defined period, e.g., by inhibition of Gsk3, and then cultured without further exogenous activation of Wnt/β-catenin signaling to obtain a cell population containing human endothelial cells.

15 Claims, 17 Drawing Sheets

FIG. 5C
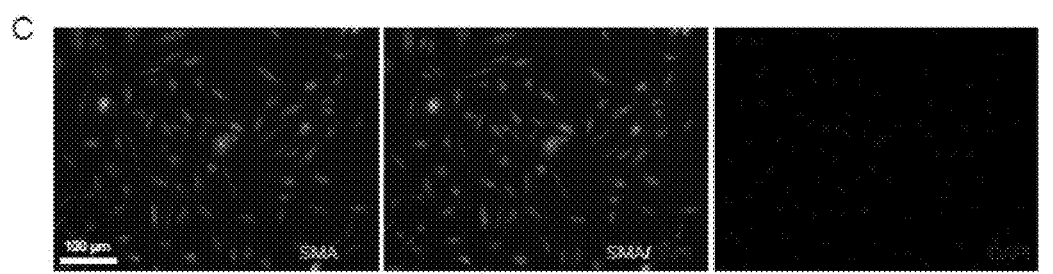
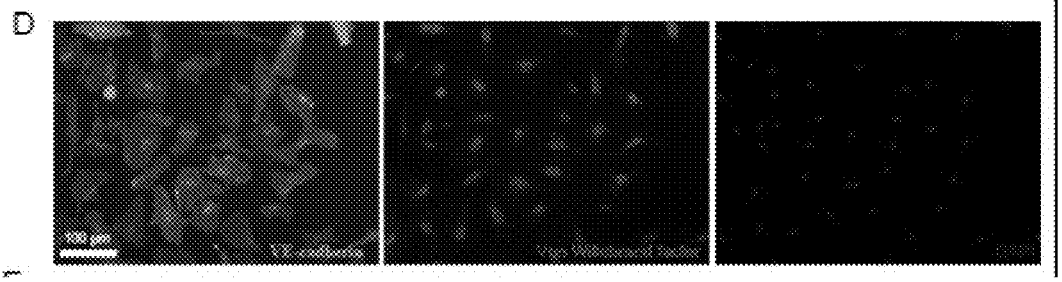
FIG. 5D

FIG. 6D
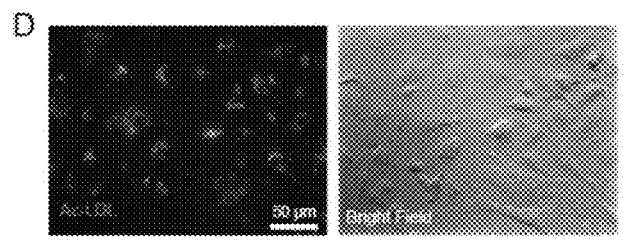
FIG. 6E
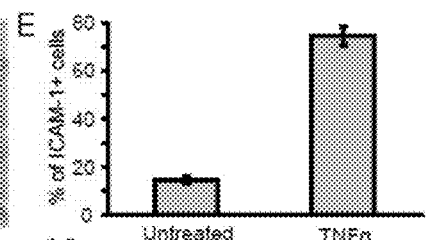
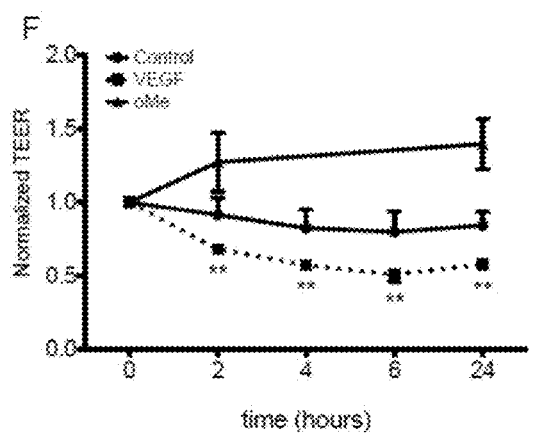
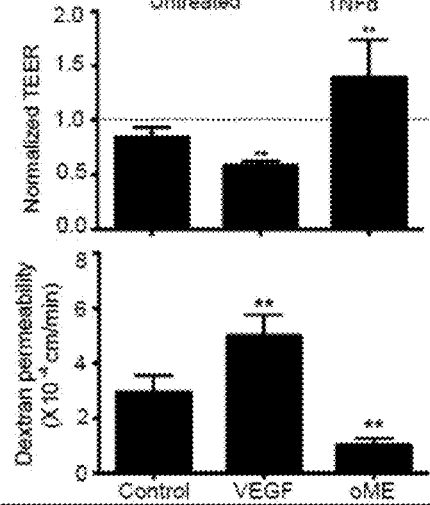
FIG. 6F
FIG. 6G

FIG. 9A
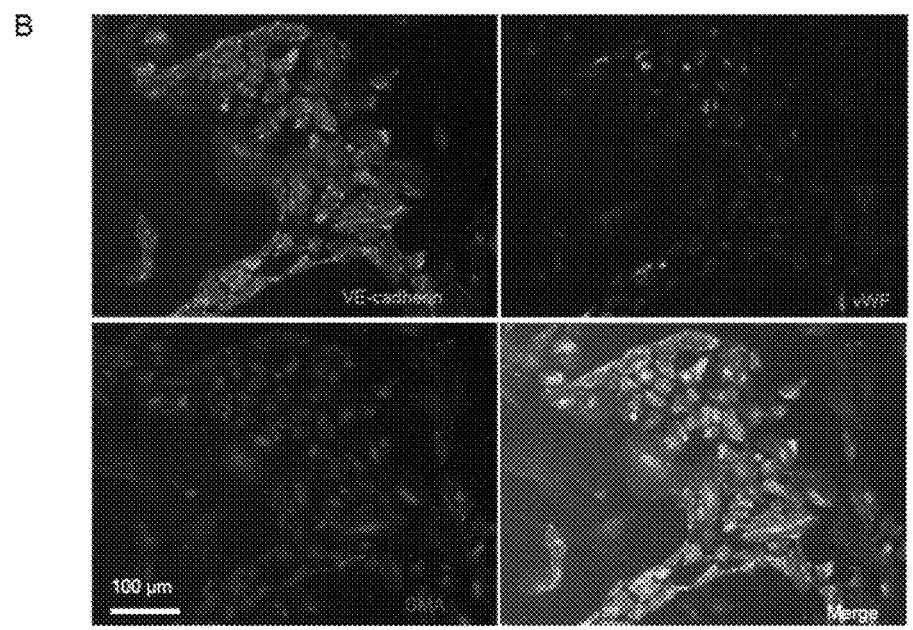
FIG. 9B

SIMPLIFIED METHODS FOR GENERATING ENDOTHELIAL CELLS FROM HUMAN PLURIPOTENT STEM CELLS UNDER DEFINED CONDITIONS

CROSS REFERENCE TO RELATED APPLICATIONS

This patent application claims priority to U.S. Provisional Patent Application Ser. No. 61/792,589 filed on Mar. 15, 2013, which incorporated by reference herein in its entirety.

STATEMENT REGARDING FEDERALLY SPONSORED RESEARCH OR DEVELOPMENT

This invention was made with government support under EB007534 awarded by the National Institutes of Health and 0735903 awarded by the National Science Foundation. The government has certain rights in the invention.

BACKGROUND

Generating endothelial cells from human pluripotent stem cells holds great promise for the development of therapies for diseases or conditions that would benefit from angiogenesis or vasculogenesis. However, endothelial development is regulated by numerous developmental pathways. Moreover, to date differentiation of human pluripotent stem cells into endothelial cells has been inefficient and required the use of expensive growth factors. Accordingly, there is a continuing need in the art for efficient, defined, and scalable methods for generating human endothelial cells from human pluripotent stem cells.

BRIEF SUMMARY

The invention relates generally to methods for differentiation of human pluripotent stem cells (hPSCs) into endothelial cells and related cell types under chemically-defined, growth factor-free conditions by activation of Wnt/β-catenin signaling for a defined period.

In one aspect provided herein is a method for generating a cell population comprising endothelial cells from human pluripotent stem cells, comprising the steps of: (i) contacting cultured human pluripotent stem cells with an activator of Wnt/β-catenin signaling for a period of about two days in a cell culture medium suitable for maintenance of human endothelial cells, but substantially free of VEGF; and (ii); obtaining a cell population comprising endothelial cells by culturing the contacted cells in the absence of the activator, for at least about three days to about ten days, in a cell culture medium suitable for maintenance of human endothelial cells but substantially free of VEGF.

In some embodiments the cultured human pluripotent stem cells are cultured at a density of about 250,000 cells/cm$^2$ to about 400,000 cells/cm$^2$ at the beginning of the contacting step.

In some embodiments the cell culture medium is selected from the group consisting of Advanced™ DMEM, VcG-Advanced™ DMEM, LaSR medium, Advanced™ DMEM F12; VcG Advanced™ DMEM-F12, StemPro® 34 medium, Advanced™ RPMI, and VcG-Advanced™ RPMI. In some embodiments the cell culture medium to be used is substantially free of exogenous growth factors. In some embodiments the cell culture medium substantially free of exogenous growth factors is LaSR medium, as described herein.

In some embodiments the activator of Wnt/β-catenin signaling is a Gsk3 inhibitor. In some embodiments the Gsk3 inhibitor is selected from the group consisting of CHIR 99021, CHIR 98014, BIO-acetoxime, BIO, LiCl, SB 216763, SB 415286, AR A014418, 1-Azakenpaullone, and Bis-7-indolylmaleimide. In some embodiments the Gsk3 inhibitor is CHIR 99021 or CHIR 98014 at a concentration of at least about 4 μM to about 10 μM in the medium. In some embodiments the Gsk3 inhibitor comprises an RNAi targeted against Gsk3.

In some embodiments the cell population obtained by the above differentiation method comprises at least 25% endothelial cells. In some embodiments, the obtained cell population comprises at least 50% endothelial cells.

In some embodiments, in step (ii) of the method, the contacted cells are cultured in the absence of the activator for about ten days.

In another aspect provided herein is a method for generating a cell population comprising CD31$^+$ cells from human pluripotent stem cells, comprising the steps of: (i) contacting cultured human pluripotent stem cells with an activator of Wnt/β-catenin signaling for a period of about two days in a cell culture medium suitable for maintenance of human endothelial cells, but substantially free of VEGF; and (ii); obtaining a cell population comprising CD31$^+$ cells by culturing the contacted cells in the absence of the activator, for about three days to about ten days, in a cell culture medium suitable for maintenance of human endothelial cells but substantially free of VEGF. In some embodiments the cell population from step (ii) is cultured for about ten days in the cell culture medium suitable for maintenance of human endothelial cells.

In some embodiments the cell population of step (ii) is subjected to selection for CD34$^+$ cells to obtain a cell population enriched for angioblasts.

In another aspect provided herein is a kit for differentiating human pluripotent stem cells into endothelial cells, comprising: (i) a Gsk3 inhibitor; (ii) a culture medium substantially free of exogenous growth factors and suitable for differentiation of human pluripotent stem cells into endothelial cells; and (iii) instructions describing a method for differentiating human pluripotent stem cells into endothelial cells, the method employing the Gsk3 inhibitor and the culture medium. In some embodiments the culture medium in the kit is selected from the group consisting of Advanced™ DMEM, VcG-Advanced™ DMEM, LaSR medium, Advanced™ DMEM F12; VcG-Advanced™ DMEM-F12, StemPro® 34 medium, Advanced™ RPMI, and VcG Advanced™ RPMI.

In another aspect provided herein is a cell culture comprising a population of human endothelial cells in a cell culture medium that is substantially free of VEGF, and supports differentiation of human pluripotent stem cells into endothelial cells.

In some embodiments at least about 25% of the cells in the cell culture are endothelial cells. In other embodiments at least about 50% of the cells in the cell culture are endothelial cells.

In some embodiments the cell culture medium in the above cell culture is selected from the group consisting of Advanced™ DMEM, VcG-Advanced™ DMEM, LaSR medium, Advanced™ DMEM F12; VcG-Advanced™ DMEM-F12, StemPro® 34 medium, Advanced™ RPMI, and VcG Advanced™ RPMI.

In yet another aspect provided herein is a population of human endothelial cells generated by a method comprising the steps of: (i) contacting cultured human pluripotent stem cells with an activator of Wnt/β-catenin signaling for a period of about two days in a cell culture medium suitable for maintenance of human endothelial cells, but substantially free of VEGF; and (ii) obtaining a cell population comprising endothelial cells by culturing the contacted cells in the absence of the activator, for at least about three days to about ten days, in a cell culture medium suitable for maintenance of human endothelial cells but substantially free of VEGF, wherein the obtained human endothelial cells will undergo at least 14 to about 20 population doublings when cultured in a culture medium suitable for proliferation of human endothelial cells. In some embodiments the contacted cells in step (ii) are cultured for about ten days. In some embodiments the cell culture medium suitable for maintenance of human endothelial cells is selected from the group consisting of Advanced™ DMEM, VcG-Advanced™ DMEM, LaSR medium, Advanced™ DMEM F12; VcG-Advanced™ DMEM-F12, StemPro® 34 medium, Advanced™ RPMI, and VcG-Advanced™ RPMI.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention from covering all modifications, equivalents and alternatives. Reference should therefore be made to the claims recited herein for interpreting the scope of the invention.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIG. 9 Generation of endothelial and smooth muscle cells from hPSC-derived-CD34$^+$ angioblasts Purified CD34 cells were generated as described in FIG. 5A and single CD34$^+$ cells were cultured in a combined medium for 10 days. Immunofluorescent staining of (A) calponin and (B) VE-cadherin/vWF/SMA were performed.

Figure 1A:
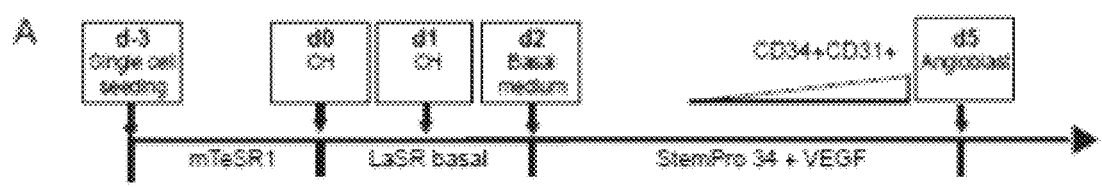
FIG. 1 Derivation of CD34$^+$CD31$^+$ cells from hPSCs via Gsk3 inhibitor treatment (A) Schematic of the protocol for differentiation of hPSCs to CD34$^+$CD31 cells via treatment with a Gsk3 inhibitor. (B) 19-9-11 iPSCs were cultured on Matrigel™ for 2 days in LaSR basal medium with or without a Gsk3 inhibitor CHIR99021 (6 µM) ("CH") followed by another 3 days in StemPro-34 medium with or without VEGF. Flow cytometry analysis of CD34 and CD31 expression after 5 days of differentiation. (C) 19-9-11 iPSCs were cultured on Matrigel™ in LaSR basal medium with different concentrations of CHIR9921 for 2 days followed by another 3 days in StemPro-34 medium. Flow cytometry analysis of CD34 and CD31 expression after 5 days of differentiation.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, preferred methods and materials are described herein.

In describing the embodiments and claiming the invention, the following terminology will be used in accordance with the definitions set out below.

As used herein, "about" means within 5% of a stated concentration range or within 5% of a stated time frame.

The terms "chemically defined culture medium," "defined culture medium," "defined medium," and the like, as used herein, indicate that the identity and quantity of each medium ingredient is known. The term "ingredient" refers to a medium component for which the identity and quantity of all constituent compounds are known. For example, a known lipid mixture containing unknown amounts of various fatty acids would not be considered a "medium ingredient" for the defined culture media described herein, whereas a lipid mixture comprising completely identified components, e.g., identified fatty acids in known proportions would be considered an "ingredient."

As used herein, the terms "chemically-defined culture conditions," "fully defined, growth factor free culture conditions," and "fully-defined conditions" indicate that the identity and quantity of each medium ingredient is known and the identity and quantity of supportive surface is known.

As used herein, "effective amount" means an amount of an agent sufficient to evoke a specified cellular effect according to the present invention.

As used herein, the term "Gsk 3 inhibited cells" refers to (i) cells in which Gsk3 has previously been inhibited, but in which Gsk3 is no longer actively inhibited; or (ii) cells in which Gsk3 is not being actively inhibited, but for which a parental stem cell or progenitor cell population was Gsk3 inhibited. Within the context of the present disclosure such "Gsk 3 inhibited cells" correspond to some embodiments in which a first cell population (comprising mesendodermal markers) is obtained after exposing human pluripotent stem cells to a Gsk3 inhibitor for a defined period of time, after which Gsk3 is no longer actively inhibited.

As used herein, the term "human pluripotent stem cell" (hPSC) means a cell capable of differentiating into cells of all three germ layers. Examples of hPSCs suitable for the methods described herein include human embryonic stem cells (hESCs) and human induced pluripotent stem cells (hiPSCs). As used herein, "iPS cells" refer to cells that are substantially genetically identical to their respective differentiated somatic cell of origin and display characteristics similar to higher potency cells, such as ES cells, as described herein. The cells can be obtained by reprogramming non-pluripotent (e.g., multipotent or somatic) cells.

As used herein, "iPS cell derivation" means reprogramming a somatic cell to become pluripotent.

As used herein, "substantially free of growth factors" refers to a medium substantially free of growth factors other than insulin.

The canonical Wnt pathway describes a series of events that occur when Wnt ligands bind to cell-surface receptors of the Frizzled family, causing the receptors to activate Dishevelled family proteins, resulting in a change in the amount of β-catenin that reaches the nucleus. Modulation of Gsk3 and Wnt pathway signaling triggers expression of a variety of developmental cues (e.g. Nodal (Kattman et al., Cell Stem Cell, 8:228-240 (2011)), BMP2/4 (Kattman et al., 2011; Laflamme et al., Nat. Biotech 25:1015-1024 (2007)), Noggin (Ma et al., Cell Res. 21:579-587 (2011)), WNT3a (Tran et al., Stem Cells, 27:1869-1878 (2009)) and WNT8a (Paige et al., PLoS One 5:e11134 (2010)).

The present invention involves a simplified method for differentiating hPSCs to obtain a cell population containing angioblasts, endothelial cells, or CD31$^+$ cell populations. In some embodiments, where endothelial cells are to be obtained, the method includes the steps of: (i) contacting cultured human pluripotent stem cells with an activator of Wnt/β-catenin signaling for a period of about two days in a cell culture medium suitable for maintenance and proliferation of endothelial cells, but substantially free of VEGF or other growth factors; and obtaining a cell population comprising endothelial cells by continued culturing of the previously contacted cells in the absence of the activator for at least three days to about ten days in a cell culture medium suitable for maintenance of human endothelial cells but substantially free of VEGF.

The methods have valuable applications such as scalable, inexpensive, and reproducible generation of human angioblasts and endothelial cells.

As disclosed herein, in contrast to previous methods in the art, exogenous vascular endothelial growth factor (VEGF) VEGF or other growth factors is not required to generate endothelial cells from human pluripotent cells, although its use is compatible with the methods described herein. As shown herein, VEGF-free directed differentiation, including temporal modulation of Wnt pathway regulators as set forth herein, can generate cell populations comprising up to about 60% endothelial cells without cell sorting or enrichment.

One advantage of the disclosed methods, differentiation of hPSCs into a differentiated population of cells comprising endothelial cells is carried out in a fully defined medium without the need for VEGF or other growth factors. Of note, unlike some methods for differentiating human pluripotent stem cells into cardiomyocytes, the methods described herein do not include a period of active inhibition of the Wnt/β-catenin signaling pathway to induce differentiation of hPSCs along the endothelial cell lineage.

As described in further detail below, the inventors' simplified protocols target key regulatory elements of the Wnt/β-catenin signaling pathway, simplifying the steps and components involved in deriving endothelial cells from human pluripotent stem cells.

In some embodiments, in the first step, i.e., step (i) of the just-mentioned method, pluripotent stem cells to be differentiated are subjected to activation of Wnt/β-catenin pathway signaling for a period of about two days.

In some embodiments, in step (ii) after the end of the Wnt/β-catenin pathway activation step, i.e., after the activator of Wnt/β-catenin pathway signaling has been removed, the (previously) contacted cells are cultured in the absence of an activator of Wnt/β-catenin pathway signaling for a period of about 10 days to obtain a cell population comprising endothelial cells.

In some embodiments disclosed herein is a method for generating $CD31^+$ cells from human pluripotent stem cells, which includes the steps of: (i) contacting cultured human pluripotent stem cells with an activator of Wnt/β-catenin signaling for a period of about two days in a cell culture medium suitable for maintenance of human endothelial cells, but substantially free of VEGF; and (ii); obtaining a cell population comprising $CD31^+$ cells by culturing the contacted cells in the absence of the activator, for about three days to about ten days, in a cell culture medium suitable for maintenance of human endothelial cells but substantially free of VEGF. As described herein, in step (ii), at about three days (5 days post-initiation of differentiation from hPSCs), a $CD31^+$ cell population is generated, which includes a transient population of $CD31^+CD34^+$VE-cadherin$^+$ angioblasts, which gives rise to $CD31^+$VE-cadherin$^+CD34^+$ endothelial cells when cultured in medium suitable for maintenance of endothelial cells as described herein.

Preferably, the hPSC cultures to be used are grown in a monolayer format such that the cell density is at least about 250,000 cells/cm$^2$ to about 400,000 cells/cm$^2$ prior to contact with an activator of Wnt/β-catenin pathway signaling, e.g., 275,000 cells/cm$^2$, 300,000 cells/cm$^2$, 325,000 cells/cm$^{2'}$ 350,000 cells/cm$^2$, 375,000 cells/cm$^2$ or another density from about 250,000 cells/cm$^2$ to about 400,000 cells/cm$^2$. In some embodiments, hPSCs to be differentiated are initially plated at a density of about 30,000 cells/cm$^2$ to about 100,000 cells/cm$^2$, e.g., 40,000 cells/cm$^2$, 50,000 cells/cm$^2$, 60,000 cells/cm$^2$, 70,000 cells/cm$^2$, 80,000 cells/cm$^2$, or another density from about 30,000 cells/cm$^2$ to about 100,000 cells/cm$^2$ and cultured for about three days prior to addition to the culture of an activator of Wnt/β-catenin pathway signaling, as described herein. Suitable culture substrates for hPSC cultures include, but are not limited to, Matrigel™, and vitronectin.

Useful nucleic acid and protein expression markers and techniques for tracking differentiation of hPSCs initially into angioblasts and subsequently into endothelial cells starting from contact of hPSCs with an activator of Wnt/β-catenin pathway signaling (Day 0) through differentiation of the hPSCs into a cell population comprising endothelial cells (Day 5), include but are not limited to the following:

Day 0: Oct4, Nanog, Sox2 (qPCR, western blot, immunostaining)

Day 1: Brachyury (qPCR, western blot), Mixl1 (qPCR), Eomes (qPCR)

Day 2: Brachyury (qPCR, western blot), Mixl1 (qPCR)

Day 3: VE-cadherin (qPCR), Brachyury (western blot)

Day 4: VE-cadherin (qPCR), CD31 (qPCR), CD34 (qPCR)

Day 5-Day 10: VE-cadherin (qPCR, western blot), CD31 (qPCR, immunostaining, flow cytometry), CD34 (qPCR, immunostaining, flow cytometry), Sox17 (qPCR), Von Willebrand factor (vWF) (western blot or immunostaining)

Angioblasts obtained as described herein are $CD31^+CD34^+$ and also express c-kit (CD117) and Tie-2. These angioblasts are multipotent, and, depending on medium conditions, generate $VE^+vWF^+$ ($CD117^-CD34^-Tie2^-$) endothelial cells or, alternatively, smooth muscle cells, which are calponin$^+$ smooth muscle myosin heavy chain (SMMC)$^+$. In some embodiments, increasing levels of endothelial cells are generated by extending culture of the initially obtained angioblast-containing cell population from day 5 (post-initiation of differentiation) onward in culture media suitable for maintenance of endothelial cells (e.g., in LaSR medium) as described herein. In other embodiments, to obtain smooth muscle cells, the angioblast-containing cell population is cultured in a cell culture medium suitable for maintenance of smooth muscle cells, e.g., SmGM™-2 medium (Lonza).

In some embodiments, angioblasts are selected from a starting population obtained at about day 5 according to the methods described herein by sorting based on CD34 expression to obtain a cell population enriched for angioblasts. In some embodiments, the enriched angioblast population comprises about 50% angioblasts to about 99% angioblasts, e.g., 60% angioblasts, 70% angioblasts, 80% angioblasts, 90% angioblasts, or another percentage of angioblasts in the enriched cell population ranging from about 50% angioblasts to 99% angioblasts.

In some embodiments, certain functional criteria for endothelial cells are also useful for confirming this cell type. Such functional criteria include, but are not limited to, the ability of the obtained cells to form endothelial tube structures when cultured on an extracellular matrix substrate (e.g., Matrigel™) upon treatment with exogenous VEGF; upregulation of E-Selectin, P-Selectin, ICAM1, or VCAM1 in response to inflammatory cytokines/stimuli, e.g., TNF-α, IL-1β, IFNγ, or LPS. Also, the obtained cells show the endothelial cell characteristic of uptake of acetylated low density lipoprotein (Ac-LDL). Other functional characteristics of the endothelial cells described herein include the responsiveness of the transendothelial electrical resistance (TEER) and macromolecular permeability to VEGF or cAMP or cAMP analogs (e.g., 8-pCPT-2'O-Me-cAMP). VEGF induces a sustained decrease in TEER and an increase in dextran permeability, whereas cAMP and analogs have the opposite effect.

As will be appreciated by those of ordinary skill in the art, Wnt/β-catenin signaling can be activated by modulating the function of one or more proteins that participate in the Wnt/

β-catenin signaling pathway to increase β-catenin expression levels or activity, TCF and LEF expression levels, or β-catenin/TCF/LEF induced transcriptional activity.

In some embodiments, activation of Wnt/β-catenin signaling is achieved by inhibition of Gsk3β ("Gsk3") phosphotransferase activity or Gsk3 binding interactions. While not wishing to be bound by theory, it is believed that inhibition of Gsk3 phosphorylation of β-catenin will inhibit tonic degradation of β-catenin and thereby increase β-catenin's level and activity to drive differentiation of pluripotent stem cells to an endodermal/mesodermal lineage. Gsk3 inhibition can be achieved in a variety of ways including, but not limited to, providing small molecule Gsk inhibitors that inhibit Gsk3 phosphotransferase activity, RNA interference knockdown of Gsk3, and overexpression of dominant negative form of Gsk3. Dominant negative forms of Gsk3 are known in the art as described, e.g., in Hagen et at (2002), *J Biol Chem*, 277 (26):23330-23335, which describes a Gsk3 comprising a R96A mutation.

In some embodiments, the Wnt/β-catenin signaling pathway is activated by inhibiting Gsk3 in pluripotent stem cells by contacting the pluripotent stem cells with a small molecule that inhibits Gsk3 phosphotransferase activity or Gsk3 binding interactions. Suitable small molecule Gsk3 inhibitors include, but are not limited to, CHIR 99021 (CAS No. 252917-06-9), CHIR 98014 (CAS No. 556813-39-9), BIO-acetoxime (CAS No. 667463-85-6), BIO (CAS No. 667463-62-9), LiCl, SB 216763 (CAS No. 280744-09-4), SB 415286 (CAS No. 264218-23-7), AR A014418 (CAS No. 487021-52-3), 1-Azakenpaullone (CAS No. 676596-65-9), Bis-7-indolylmaleimide (CAS No. 133052-90-1), and any combinations thereof. In some embodiments, any of the foregoing Gsk3 inhibitors are used at a concentration of at least about 500 to about 1000 times their $IC_{50}$ for isolated Gsk3 activity in vitro. In some embodiments, any of CHIR 99021, CHIR 98014, and BIO-acetoxime are used to inhibit Gsk3 in pluripotent stem cells in the differentiation methods described herein. In one embodiment, the small molecule Gsk3 inhibitor to be used is CHIR99021 at a concentration ranging from about 3 µM to about 15 µM, e.g., about 4 µM, 5 µM, 6 µM, 8 µM, 10 µM, 12 µM, or another concentration of CHIR99021 from about 3 µM to about 15 µM. In another embodiment, the small molecule Gsk3 inhibitor to be used is CHIR 98014 at a concentration ranging from about 4.0 µM to about 8.0 µM, e.g., about 4.5 µM, 5.0 µM, 5.5 µM, 6.0 µM, 6.7 µM, 7.0 µM, or another concentration of CHIR99021 from about 4.0 µM to about 8.0 µM.

In other embodiments, Gsk3 activity is inhibited by RNA interference knockdown of Gsk3. For example, Gsk3 expression levels can be knocked-down using commercially available siRNAs against Gsk3, e.g., SignalSilence® GSK3α/β siRNA (catalog #6301 from Cell Signaling Technology®, Danvers, Mass.), or a retroviral vector with an inducible expression cassette for Gsk3, e.g., a commercially available Tet-inducible retroviral RNAi system from Clontech (Mountain View, Calif.) Catalog No. 630926, or a cumate-inducible system from Systems Biosciences, Inc. (Mountain View, Calif.), e.g., the SparQ® system, catalog no. QM200PA-2.

In other embodiments, the Wnt/β-catenin signaling pathway is activated by overexpressing β-catenin itself, e.g., human β-catenin (GenBank Accession Nos: X87838 and CAA61107.1 for nucleotide and protein sequences, respectively). In one embodiment, β-catenin overexpression is inducible β-catenin overexpression achieved using, e.g., any of the just-mentioned inducible expression systems. Alternatively, a constitutively active, stabilized isoform of β-catenin is used, which contains point mutations S33A, S37A, T41A, and S45A as described, e.g., in Baba et at (2005), *Immunity*, 23(6):599-609.

In yet other embodiments, Wnt/β-catenin signaling pathway activation in pluripotent stem cells is achieved by contacting the cells with an agent that disrupts the interaction of β-catenin with Axin, a member of the β-catenin destruction complex. Disruption of Axin-β-catenin interaction allows β-catenin to escape degradation though the destruction complex thereby increasing the net level of β-catenin to drive β-catenin signaling. For example, the Axin-β-catenin interaction can be disrupted in pluripotent cells by contacting them with the compound 5-(Furan-2-yl)-N-(3-(1H-imidazol-1-yl)propyl)-1,2-oxazole-3-carboxamide ("SKL2001"), which is commercially available, e.g., as catalog no. 681667 from EMD4 Biosciences. An effective concentration of SKL2001 to activate Wnt/β-Catenin signaling ranges from about 10 µM to about 100 µM, about 20 µM, 30 µM, 40 µM, 50 µM, 60 µM, 70 µM, 80 µM, 90 µM or another concentration of SKL2001 from about 10 µM to about 100 µM.

Defined media and substrate conditions for culturing pluripotent stem cells, as used in the methods described herein, are well known in the art. In some exemplary embodiments, pluripotent stem cells to be differentiated according to the methods disclosed herein are cultured in mTESR-1® medium (StemCell Technologies, Inc., Vancouver, Calif.), or Essential 8® medium (Life Technologies, Inc.) on a Matrigel™ substrate (BD Biosciences, NJ) according to the manufacturer's protocol or on a Corning® Synthemax surface.

Upon initiating the first step and throughout the differentiation period of the methods described herein, pluripotent cells are cultured in a medium substantially free of VEGF. In other embodiments, the medium to be used is substantially free of growth factors. Suitable culture media include, but are not limited to, Advanced™ DMEM (Life Technologies, Cat. No. 12491-015), Advanced™ DMEM-F12 (Life Technologies, Cat. No. 12634-010), Advanced™ RPMI 1640 (Life Technologies, Cat. No. 12633-012), and StemPro®34 (Life Technologies, Cat. No. 10639-011).

In some embodiments, the medium to be used includes supplemental ascorbate (AKA "vitamin C") such that the final concentration of ascorbate (including ascorbate present in the base medium) in the medium is about 0.2 mM; and is supplemented with GlutaMAX™ (Life Technologies) at a final concentration of about 2.5 mM. Media comprising supplemental ascorbate and GlutaMAX™ are referred to herein as "VcG-media," e.g., "VcG-Advanced™ DMEM" medium. In preferred embodiments, the medium to be used is VcG-Advanced™ DMEM-F12 medium referred to herein as "LaSR" medium.

Also described herein are kits useful for differentiating hPSCs into endothelial cells. In some embodiments, a kit contains: (i) a Gsk3 inhibitor; (ii) a culture medium substantially free of VEGF or substantially free of growth factors and suitable for differentiation of human pluripotent stem cells into endothelial cells; and (iii) instructions describing a method for differentiating human pluripotent stem cells into endothelial cells comprising contacting the human pluripotent stem cells for a period of about two days with the Gsk3 inhibitor while cultured in the culture medium; and culturing the contacted cells, in the absence of the Gsk3 inhibitor, in the medium for at least about three days to obtain a population of cells comprising at least 25% endothelial cells.

Suitable media for use in the kit include, but are not limited to, Advanced™ DMEM, VcG-Advanced™ DMEM, LaSR medium, Advanced™ DMEM-F12; VcG-Advanced™ DMEM-F12, StemPro® 34 medium, Advanced™ RPMI, and VcG-Advanced™ RPMI. In one embodiment, the medium to be included in the kit is LaSR medium.

Suitable Gsk3 inhibitors for the kit include, but are not limited to, CHIR 99021, CHIR 98014, BIO-acetoxime, BIO, LiCl, SB 216763, SB 415286, AR A014418, 1-Azakenpaullone, and Bis-7-indolylmaleimide.

In some embodiments, continued culture and differentiation of the cell population, in the absence of VEGF or other growth factors, after ending Wnt/β-catenin signaling activation yields a cell population comprising about 5% to about 60% endothelial cells, e.g., about 7%, 10%, 15%, 20%, 24%, 30%, 35%, 40%, 45%, 50%, or another percent of endothelial cells from about 5% to about 60%.

Accordingly, provided herein is a cell culture that contains a population of viable human endothelial cells in a cell culture medium substantially free of VEGF, and supports differentiation of human pluripotent stem cells into endothelial cells. In some embodiments, the cell culture comprises a cell culture medium that is substantially free of growth factors.

After obtaining a cell population comprising human endothelial cells according to a VEGF or growth-factor-free differentiation method as described herein, the proportion of endothelial cells may be further enriched using a cell separation or enrichment method, e.g., FACS, MACS, or laser-targeted ablation of non-endothelial cells. In some embodiments, human endothelial cells are selected based on surface expression of CD31, e.g., by MACS. After enrichment, the resulting cell population comprises at least about 90% to about 100%, e.g., about 92%, 93%, 95%, 96%, 99%, or another percent of human endothelial cells from about 90% to about 100% of the enriched cell population. In some embodiments, at about day 5, a population of angioblasts is purified based on expression of CD34, and subsequently cultured under conditions favorable to endothelial cells, as described herein, to obtain a highly enriched population of $CD31^+VE$-cadherin$^+CD34^+$ endothelial cells (derived from the angioblasts) by about day 10.

After enrichment for endothelial cells, the human endothelial cells obtained by the described differentiation methods can be expanded in any of a number of known media useful for proliferation of human endothelial cells, including, but not limited to Human Endothelial Serum-Free Medium (Life Technologies, Cat. No. 11111-044), EGM-2 (Lonza, Cat. No. CC-3162), and Endothelial Cell Culture Medium (BD Biosciences, Cat. No. 355054).

The populations of human endothelial cells obtained by the differentiation methods described herein are characterized by their ability to proliferate and expand far more than usual compared to primary human endothelial cells and endothelial cells differentiated from hPSCs by methods other than the ones described herein. In some embodiments, the population of cells obtained by the present differentiation method, when further cultured in a culture medium suitable for proliferation of human endothelial cells, will undergo at least about 14 population doublings in a period of about 25 days, which is approximately a 16,000 fold expansion of the starting population. In some embodiments, the just mentioned populations of human endothelial cells undergo at least 14 doublings to about 20 doublings, e.g., 15, 16, 17, 18, 19, or 20 doublings, which are a greater number of doublings than expected for primary human endothelial cells under the same culture conditions.

The invention will be more fully understood upon consideration of the following non-limiting Examples. It is specifically contemplated that the methods disclosed are suited for pluripotent stem cells generally. All papers and patents disclosed herein are hereby incorporated by reference as if set forth in their entirety.

EXAMPLES

Example 1

Gsk3 Inhibition is Sufficient to Induce hPSC Differentiation to Angioblasts in the Absence of Exogenous Growth Factors Materials and Methods
Maintenance of hPSCs Transgene and vector free human iPSCs (19-9-11)[53] and hESCs (H1, H9)[54] were maintained on Matrigel™ (BD Biosciences) coated plates (Corning) in mTeSR1 medium (STEMCELL Technologies) according to a previously published method[39].

Angioblast Differentiation Via Modulation of Canonical Wnt Signaling hPSCs maintained on a Matrigel™-coated surface in mTeSR1 were dissociated into single cells with Accutase (Life Technologies) at 37° C. for 5 min and then seeded onto a Matrigel™-coated cell culture dish at 50,000 cell/cm² in mTeSR1 supplemented with 5 µM ROCK inhibitor Y-27632 (Selleckchem)(day −3) for 24 hours. Cells were then cultured in mTeSR1, changed daily. At day 0, cells were treated with 6-10 µM CHIR99021 (Selleckchem) for 2 days in LaSR basal medium, which consists of Advanced DMEM/F12, 2.5 mM GlutaMAX, and 60 µg/ml ascorbic acid (Sigma, A8960). After 2 days, CHIR99021-containing medium was aspirated and cells were maintained in LaSR basal medium without CHIR99021 for 3 to 4 additional days.

Differentiation of CD34$^+$ to Endothelial Cells

Day 5 differentiated populations were dissociated with Accutase for 10 min and purified with an EasySep Magnet kit (STEMCELL Technologies) using a CD34 antibody according to the manufacturer's instructions. The purified CD34 cells were plated on collagen IV-coated dishes (BD BioCoat) in EGM-2 medium (Lonza) and split every 4-5 days with Accutase.

Differentiation of CD34$^+$ to Smooth Muscle Cells

Day 5 differentiated populations were dissociated with Accutase for 10 min and purified with an EasySep Magnet kit (STEMCELL Technologies) using a CD34 antibody according to the manufacturer's instructions. The purified CD34 cells were plated on collagen IV-coated dishes (BD BioCoat) in SmGM-2 medium (Lonza) and split every 4-5 days with Accutase.

Vascular Tube Formation Assay

To assess the formation of capillary structures, $1\times10^5$ endothelial cells in 0.4 ml EGM-2 medium (Lonza) supplemented with 50 ng/ml VEGF (R&D Systems) were plated into one well of 24-well tissue culture plate pre-coated with 250 µl Matrigel™ (BD Bioscience). Tube formation was observed by light microscopy after 24 h of incubation.

RT-PCR and Quantitative RT-PCR

Total RNA was prepared with the RNeasy mini kit (QIAGEN) and treated with DNase (QIAGEN). 1 µg RNA was reverse transcribed into cDNA via Oligo (dT) with Superscript III Reverse Transcriptase (Invitrogen). Real-time quantitative PCR was done in triplicate with iQSYBR Green SuperMix (Bio-Rad). RT-PCR was performed with Gotaq Master Mix (Promega) and then subjected to 2% agarose gel electrophoresis. ACTB was used as an endogenous housekeeping control. PCR primer sequences are provided in Table 1.

Flow Cytometry

Cells were dissociated into single cells with Accutase for 10 min and then fixed with 1% paraformaldehyde for 20 min at room temperature and stained with primary and secondary antibodies (Table 2) in PBS plus 0.1% Triton X-100 and 0.5%

BSA. Data were collected on a FACSCaliber flow cytometer (Becton Dickinson) and analyzed using FlowJo.

Immunostaining

Cells were fixed with 4% paraformaldehyde for 15 min at room temperature and then stained with primary and secondary antibodies (Table S2) in PBS plus 0.4% Triton X-100 and 5% non-fat dry milk (Bio-Rad). Nuclei were stained with Gold Anti-fade Reagent with DAPI (Invitrogen). An epifluorescence microscope (Leica DM IRB) with a QImaging® Retiga 4000R camera was used for imaging analysis.

Western Blot Analysis

Cells were lysed in M-PER Mammalian Protein Extraction Reagent (Pierce) in the presence of Halt Protease and Phosphatase Inhibitor Cocktail (Pierce). Proteins were separated by 10% Tris-Glycine SDS/PAGE (Invitrogen) under denaturing conditions and transferred to a nitrocellulose membrane. After blocking with 5% dried milk in TBST, the membrane was incubated with primary antibody overnight at 4° C. The membrane was then washed, incubated with an anti-mouse/rabbit peroxidase-conjugated secondary antibody (Table 2) at room temperature for 1 hr, and developed by SuperSignal chemiluminescence (Pierce).

Monolayer Integrity

Purified CD31+ endothelial cells were seeded on 12-well plate size 0.4 μm porous polystyrene membrane inserts (Transwells, Corning, N.Y.) coated with a 0.4 mg/mL collagen IV and 0.1 mg/mL fibronectin mixture at a density of 250,000 cells/insert. Cells were maintained in endothelial cell SFM (Life Technologies) for 48 hrs prior to addition 0.5 ml and 1.5 ml of endothelial SFM at the apical and basolateral chambers respectively. Barrier tightness was assessed by measurement of transendothelial electrical resistance (TEER) using a EVOM STX2 electrode system (World Precision Instruments, Sarasota, Fla.) before medium replacement. Baseline resistance values served to normalize subsequent TEER measurements. Cells were treated with either 100 ng/ml VEGF or 10 μM 8-(4-chlorophenylthio)-2'-O-Me-cAMP (oMe). TEER measurements were acquired every two hr, with the exception of oME-treated cells. After 24 hr of treatment, vascular permeability was assessed by replacing the medium in the top chamber with 500 μl of 1 μM 40-kDa FITC-dextran (Sigma-Aldrich) dissolved in endothelium SFM. At 15, 30, 45 and 60 min, 150 μl aliquots were taken from the basolateral chamber and replaced with warm endothelial SFM. Cell permeability was calculated following the Pe clearance method[55,56].

Statistics

Data are presented as mean±standard error of the mean (SEM). Statistical significance was determined by Student's t-test (two-tail) between two groups. P<0.05 was considered statistically significant.

TABLE 1

Primer Sequences for Q-PCR

| Genes | | Sequences (5'-3') | Size (bp)/ Tm (° C.) |
|---|---|---|---|
| OCT4 | F: | CAGTGCCCGAAACCCACAC (SEQ ID NO: 1) | 161/58 |
| | R: | GGAGACCCAGCAGCCTCAAA (SEQ ID NO: 2) | |
| SOX2 | F: | CAAGATGCACAACTCGGAGA (SEQ ID NO: 3) | 300/58 |
| | R: | GTTCATGTGCGCGTAACTGT (SEQ ID NO: 4) | |
| MIXL1 | F: | CAGAGTGGGAAATCCTTCCA (SEQ ID NO: 5) | 231/58 |
| | R: | TGAGTCCAGCTTTGAACCAA (SEQ ID NO: 6) | |
| CD31 | F: | GCTGACCCTTCTGCTCTGTT (SEQ ID NO: 7) | 238/55 |
| | R: | TGAGAGGTGGTGCTGACATC (SEQ ID NO: 8) | |
| CD34 | F: | CCTAAGTGACATCAAGGCAGAA (SEQ ID NO: 9) | 201/55 |
| | R: | GCAAGGAGCAGGGAGCATA (SEQ ID NO: 10) | |
| ACTB | F: | CCTGAACCCTAAGGCCAACCG (SEQ ID NO: 11) | 400/58 |
| | R: | GCTCATAGCTCTTCTCCAGGG (SEQ ID NO: 12) | |
| GAPDH | F: | GTGGACCTGACCTGCCGTCT (SEQ ID NO: 13) | 152/58 |
| | R: | GGAGGAGTGGGTGTCGCTGT (SEQ ID NO: 14) | |
| T | F: | AAGAAGGAAATGCAGCCTCA (SEQ ID NO: 15) | 101/58 |
| | R: | TACTGCAGGTGTGAGCAAGG (SEQ ID NO: 16) | |
| CTNNB1 | F: | CCCACTAATGTCCAGCGTTT (SEQ ID NO: 17) | 217/58 |
| | R: | AACGCATGATAGCGTGTCTG (SEQ ID NO: 18) | |

TABLE 2

Antibodies for immunostaining (IS), western blotting (WB) and flow cytometry (FC)

| Antibody | | Application |
|---|---|---|
| CD31-APC | Miltenyi Biotec, mouse IgG1, Clone: AC128 Cat. no: 130-092-652 | 1:50 (FC) |
| CD34-FITC | Miltenyi Biotec, mouse IgG2a, Clone: AC136 Cat. no: 130-081-001 | 1:50 (FC) |
| Brachyury | R&D Polyclonal Ab, GoatIgG Clone: AF2085 | 1:100 (FC) 1:1000 (WB) |
| VE-cadherin | Santa Cruz, mouse IgG1, Clone: F-8 sc9989 | 1:100 (IS) 1:1000 (WB) |
| Oct-3/4 | Santa Cruz, Mouse IgG2b Clone: C-10 sc-5279 | 1:100 (IS) 1:1000 (WB) |
| SMMHC | Abcam 82541, RabbitIgG, Cat. no: 82541 | 1:800 (IS) |
| Actin, smooth muscle | Thermo Scientific, mouse IgG2a/κ Clone: 1A4 MS-113-P | 1:100 (IS) |
| CD117 (c-kit) | BD Pharmingen, mouse IgG1/κ Clone: YB5.B8 Cat. no: 555713 | 1:200 (IS) |
| Tie-2 | Santa Cruz, rabbit IgG, Clone: H-176 sc9026 | 1:200 (IS) |
| KDR | Santa Cruz, mouse IgG1, Clone: A-3 sc6251 | 1:200 (IS) |

TABLE 2-continued

Antibodies for immunostaining (IS), western blotting (WB) and flow cytometry (FC)

| Antibody | | Application |
|---|---|---|
| vWF | Dako, rabbit IgG, Cat. no: A008202-5 | 1:500 (IS) |
| ICAM-1 (CD54) | DSHB, mouse IgG1, P2A4 | 1:30 (IS) |
| Calponin | Abcam, Mouse IgG1, Clone: CALP Cat. no: ab700 | 1:200 (IS) |
| β-Actin | Cell Signaling Technology, Rabbit mAb (HRP Conjugate), 13E5, 5125S | 1:5000 (WB) |
| goat anti-mouse IgG-HRP | Santa Cruz, sc-2005 | 1:3000 (WB) |

Figure 1B:
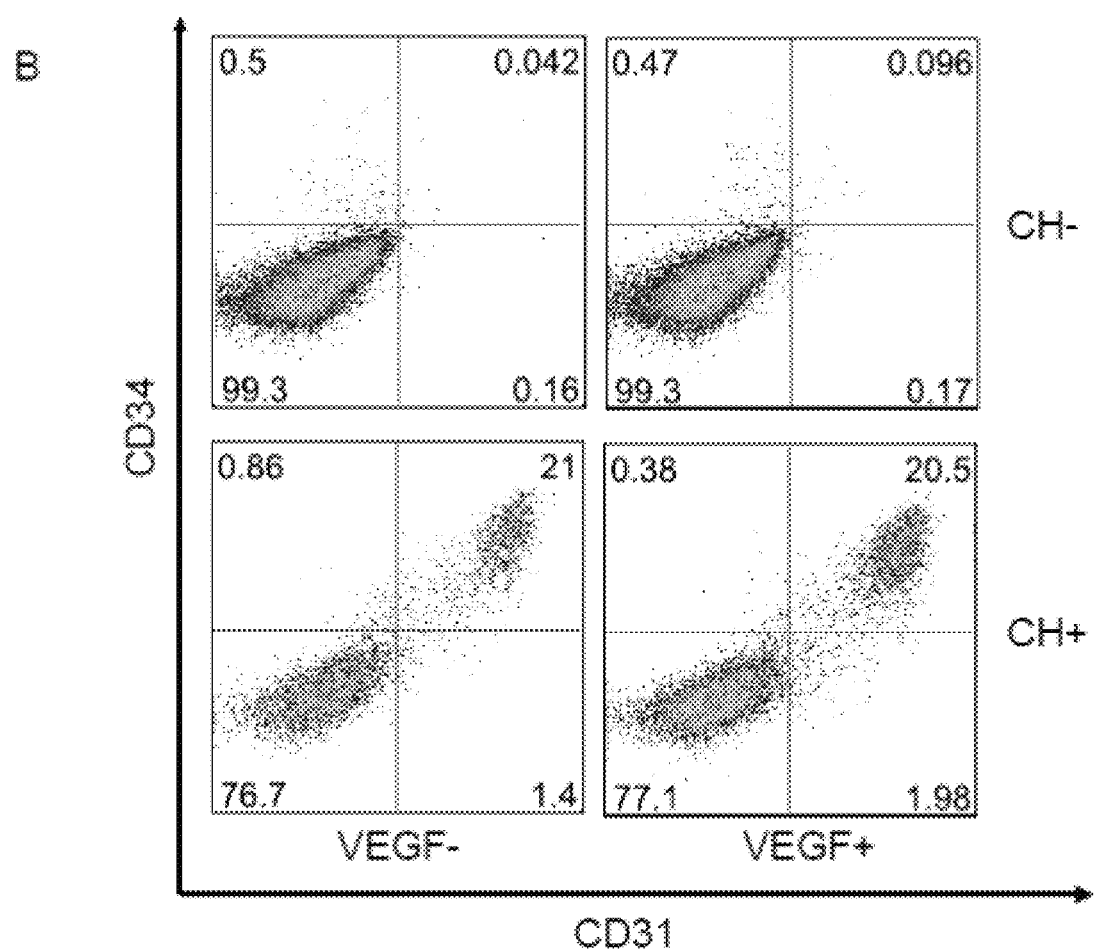

We previously demonstrated that temporal modulation of canonical Wnt signaling is sufficient to generate functional cardiomyocytes at high yield and purity[35,36]. In that study, a virtually pure population of Brachyury+ cells was generated within 24 hours after treatment of undifferentiated hPSCs with a Gsk3 inhibitor. In order to direct these Brachyury+ cells to a cardiomyocyte fate, we then inhibited canonical Wnt signaling by either expression of β-catenin shRNA or treatment with small-molecule inhibitors of Wnt signaling at the proper corresponding time points. To assess whether these Gsk3 inhibitor-induced Brachyury+ mesendoderm progenitors also have the potential to differentiate to the angioblast lineage, we treated 19-9-11 iPSCs with the Gsk3 inhibitor CHIR99021 and subsequently cultured the cells in StemPro-34 medium supplemented with VEGF, both of which have been reported to stimulate vascular cell differentiation of hPSCs[37] (FIG. 1A). After optimizing the concentrations and timing of application of various components, the differentiation protocol consisted of two phases. Phase I generates Brachyury+ cells by treatment of undifferentiated hPSCs with CHIR990211 for two days while phase II directs the Brachyury+ progenitors to CD34+CD31+ cells by culture in StemPro-34 supplemented with VEGF for three days. We found that without CHIR99021 treatment, very few CD34+CD31+ cells were generated from human iPSCs, even in the presence of VEGF (FIG. 1B). However, treatment of the human iPSCs with CHIR99021 generated more than 20% CD34+CD31+ cells. Interestingly, VEGF treatment did not significantly increase the yield of CD34+CD31+ cells in this differentiation system (FIG. 1B). Because of this observation, we did not include VEGF in subsequent differentiation experiments. In addition, this differentiation protocol primarily generated CD34+CD31+ cells and produced very few CD34−CD31+ or CD34+CD31− cells (FIG. 1B).

Figure 1C:
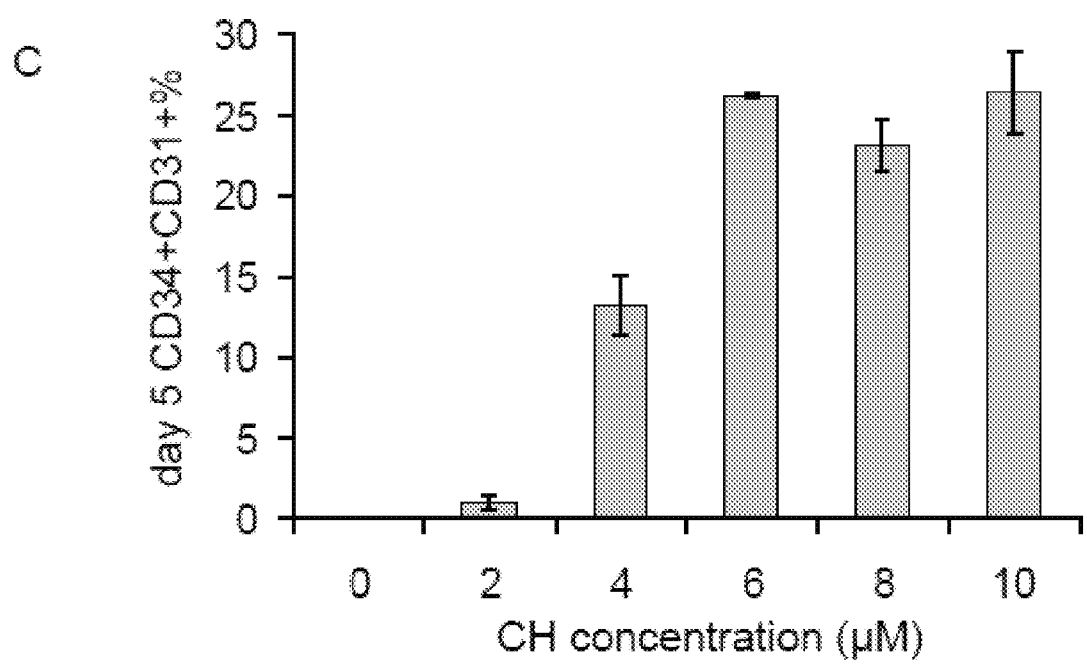
Figure 7:
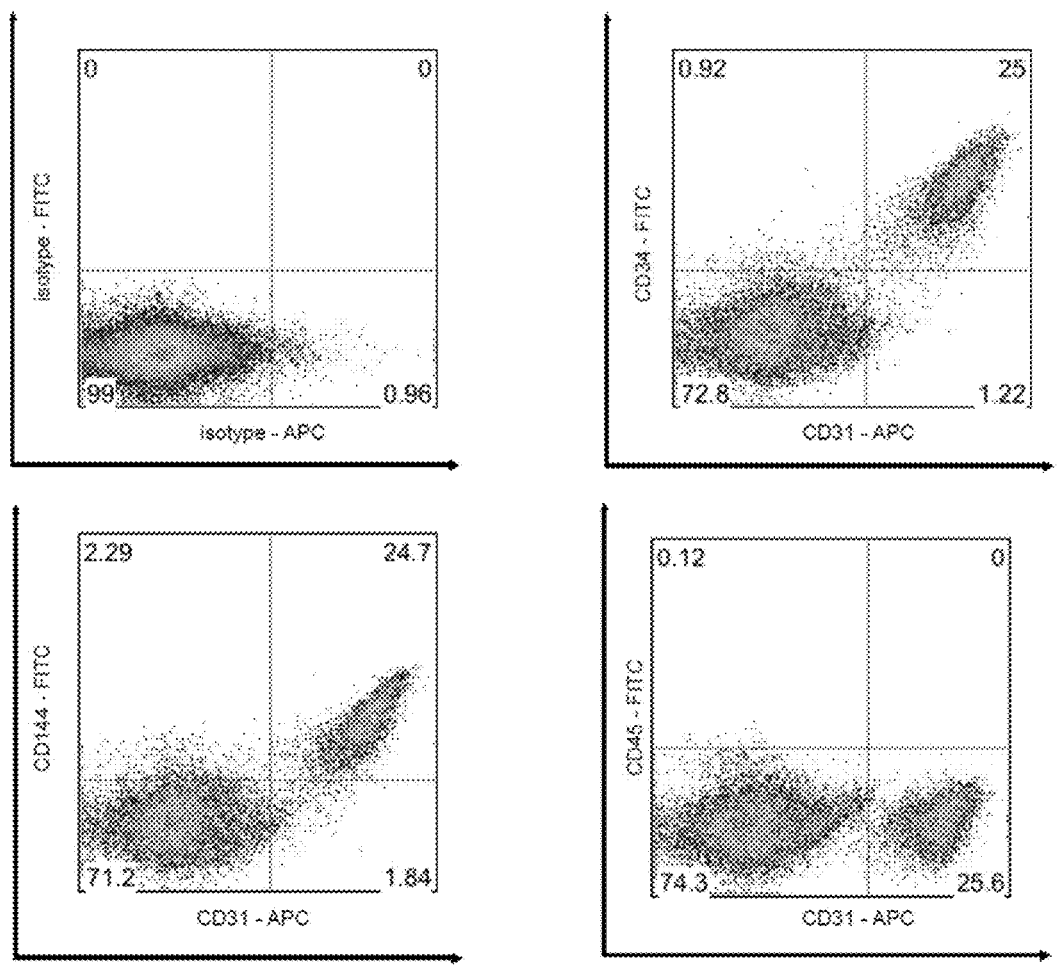
FIG. 7 Flow cytometry analysis of cells obtained by endothelial differentiation of hPSCs H1 Human embryonic stem cells were cultured on Matrigel™ in LaSR basal medium containing 6 µM CHIR99021 for two days followed by another 3 days in Stem-Pro® 34 medium. Flow cytometry analysis of CD34 and CD31, CD31 and CD144, CD31 and CD45 expression was performed after 5 days of differentiation.

We further tested the concentration dependence of CHIR99021 for inducing CD31+CD34+ angioblast differentiation and found that 6-10 μM generated 25% angioblasts (FIG. 1C). Similar results were obtained in the H1 human embryonic stem cell (hESC) line (FIG. 7). These CD34+CD31+ angioblasts also expressed CD144 (VE-Cadherin), but not CD45, indicating these cells were not in hematopoietic lineages (FIG. 7). These results illustrate that induction of Wnt signaling via the Gsk3 inhibitor CHIR99021 permits differentiation of hPSCs intoCD34+CD31+ cells differentiation of hPSCs, and that exogenous VEGF is not required for this differentiation.

Example 2

Figure 2A:
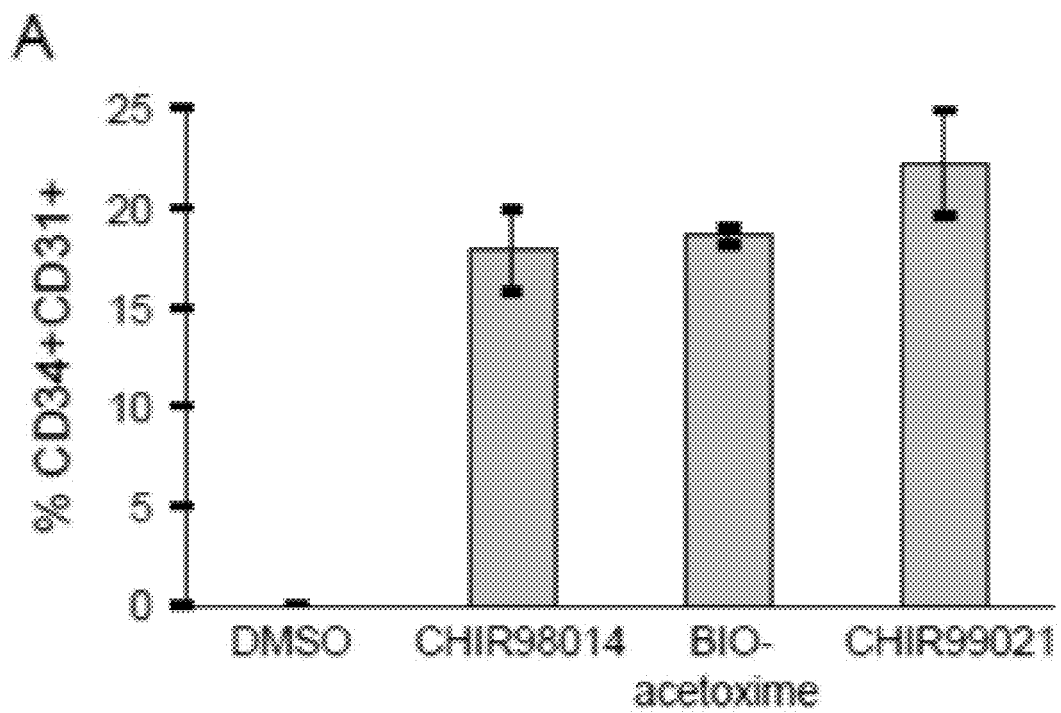
FIG. 2 CD34$^+$CD31$^+$ angioblast differentiation induced by Gsk3 inhibitors in hPSCs is β-catenin dependent. (A) 19-9-11 iPSCs were cultured on Matrigel™ in LaSR medium containing DMSO, 0.6 µM CHIR98014, 0.6 µM BIO-acetoxime, or 6 µM CHIR99021 for 2 days before culture in StemPro-34 medium for 3 days. At day 5, the percentage of CD34$^+$CD31$^+$ cells in culture was assessed by flow cytometry. (B) 19-9-11 iscramble and 19-9-11 ishcat cells were cultured in mTeSR1 containing 2 µg/ml doxycycline. After 3 days, mRNA was collected and β-catenin expression evaluated by qPCR. Error bars represent the s.e.m. of 3 biological replicates. # p<0.005, ishcat versus iscramble; t test. (C) 19-9-11 ishcat cells were cultured in LaSR medium containing 6 µM CHIR99021 for 2 days before exposure to StemPro-34 medium for 3 days, with 2 µg/ml dox addition at the indicated times. 5 days after initiation of differentiation, cells were analyzed for CD34 and CD31 expression by flow cytometry. Error bars represent the s.e.m. of three independent experiments. (D) H9 cells were cultured in LaSR medium containing 6 µM CHIR99021 for 2 days before exposure to StemPro-34 medium for 3 days, with 1 µM PD0325901 addition at the indicated times. 5 days after initiation of differentiation, cells were analyzed for CD34 and CD31 expression by flow cytometry.
Figure 2B:
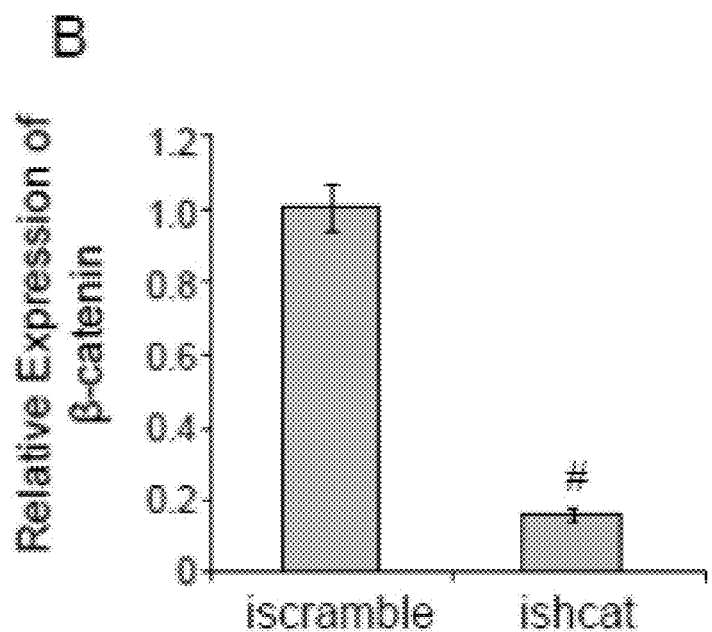
Figure 2C:
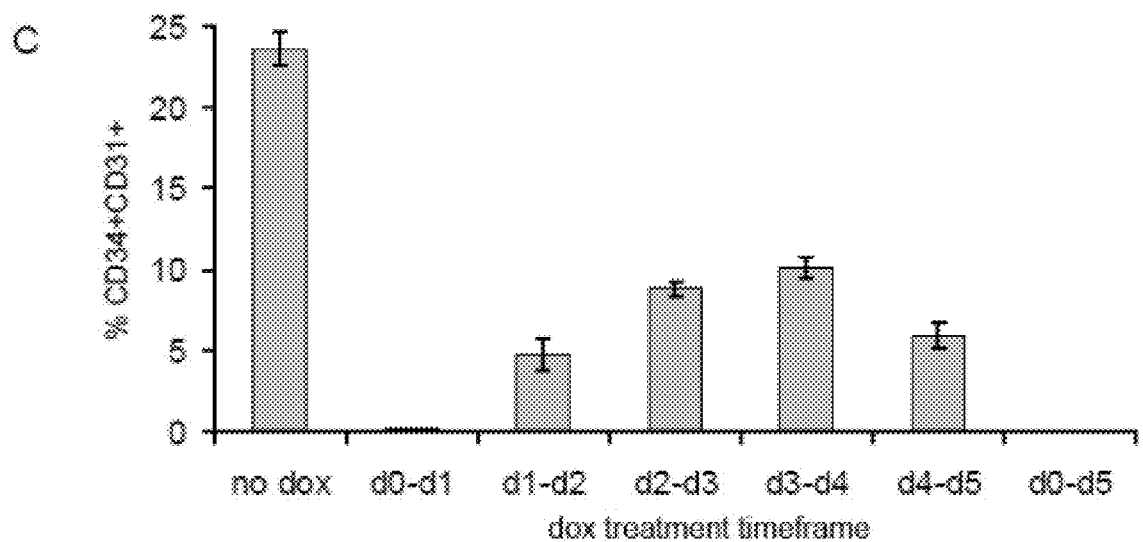
Figure 2D:
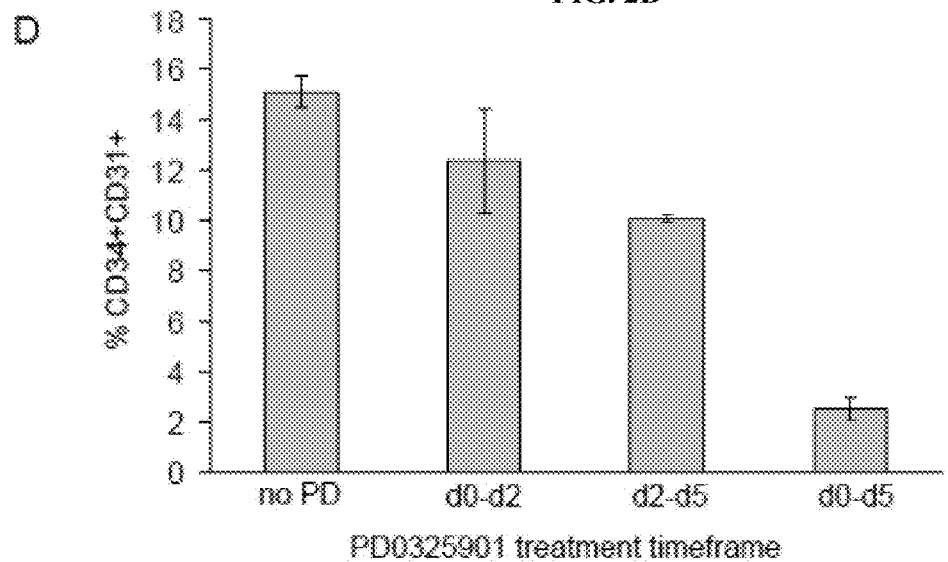
Figure 8:
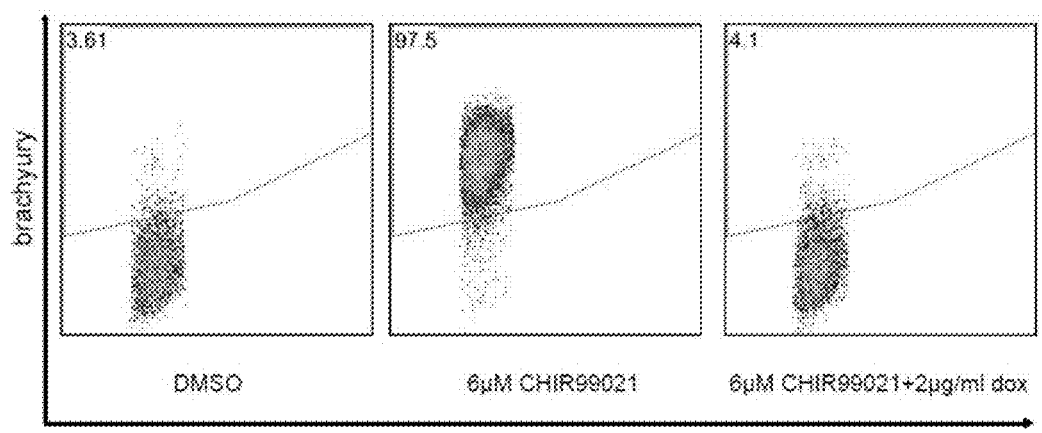
FIG. 8 Knockdown of β-catenin abolishes endothelial differentiation of hPSCs 19-9-11 ishcat iPSCs were cultured in LaSR basal medium containing 6 µM CH and/or 2 µg/ml doxycycline for 2 days. Flow cytometry analysis of Brachyury expression was performed after 2 days of differentiation.

Angioblast Differentiation Induced by Gsk3 Inhibitors in hPSCs is β-Catenin Dependent Selectivity is a general concern with the use of chemical inhibitors. We tested other Gsk3 inhibitors, BIO-acetoxime and CHIR98014, and found that both also effectively induced angioblast differentiation to a similar extent as CHIR99021 in the absence of VEGF treatment (FIG. 2A). These small molecule compounds have distinct chemical structures, reducing the likelihood of shared off-target effects. However, Gsk3 inhibition can affect multiple signaling pathways, including the desired activation of canonical Wnt signaling by stabilizing β-catenin protein. In order to evaluate the role of β-catenin in Gsk3 inhibitor-induced hPSC endothelial differentiation, we generated an iPSC line (19-9-11 ishcat-1) expressing β-catenin shRNA under the control of a tet-regulated inducible promoter. Upon doxycycline (dox) addition, the shRNA efficiently downregulated β-catenin expression (FIG. 2B). We used this cell line to examine the stage-specific roles of β-catenin during monolayer endothelial differentiation stimulated by Gsk3 inhibition. Undifferentiated 19-9-11 ishcat-1 iPSCs were treated with 6 μM CHIR99021 for 48 hours followed by another 3 days culture in StemPro-34 medium. Dox was added at various time points between day 0 and day 4, and angioblast differentiation was assessed at day 5 as the percentage of CD34+CD31+ cells. We found that Wnt/β-catenin signaling was essential for endothelial induction by CHIR99021 since β-catenin knockdown at day 0 did not generate CD34+CD31+ cells. We previously showed that β-catenin is essential for Brachyury expression after hPSC treatment with Gsk3 inhibitors35. We reasoned that abrogation of the CD34+CD31+ population by β-catenin knockdown at day 0 was due to blocking differentiation of hPSCs to Brachyury-expressing mesendoderm progenitors. We profiled the expression of Brachyury during the 5 day differentiation and found a virtually pure population of Brachyury cells generated by day 2 in the absence of dox. The presence of dox treatment, however, abolished Brachyury expression (FIG. 8). Importantly, depletion of β-catenin expression at time points after Brachyury expression was detected also reduced the percentage of CD34+CD31+ cells generated (FIG. 2C), indicating β-catenin might also be involved in mesendoderm to CD34+CD31+ cell differentiation. Because of the important role of FGF2 signaling on Brachyury+ cell differentiation from hPSCs[38] and the mesodermal origin of angioblasts, we used an FGF inhibitor to study the role of endogenous FGF signaling on CD34+CD31+ cell differentiation. We found that the FGF2 inhibitor PD0325901 substantially diminished CD34+CD31+ cell differentiation, suggesting that endogenous FGF2 signaling promotes angioblast differentiation (FIG. 2D).

Example 3

Figure 3A:
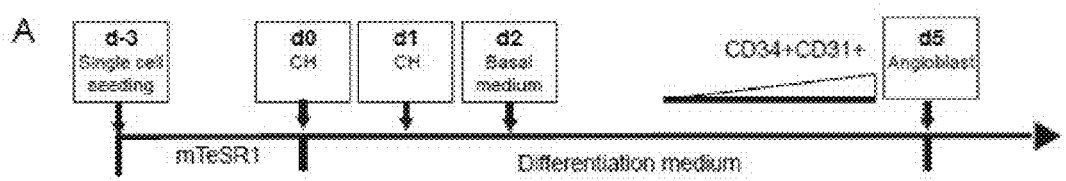
FIG. 3 Differentiation medium and cell density dependence of Gsk3 inhibitor-induced angioblast differentiation (A) Schematic of the protocol for defined, growth factor-free differentiation of hPSCs to angioblasts in a single differentiation medium. (B) 19-9-11 iPSCs were cultured as indicated in (A), with different basal differentiation media. At day 5, cells were analyzed for CD34 and CD31 expression by flow cytometry. Error bars represent the s.e.m. of three independent experiments. p=0.02, LaSR basal versus StemPro 34; t test. (C-D) 19-9-11 iPSCs were differentiated as described in (A) using LaSR basal medium, with different day –3 cell seeding densities. (C) At day 5, cells were analyzed for CD34 and CD31 expression by flow cytometry. Error bars represent the s.e.m. of three independent experiments. (D) One representative CD34/CD31 flow plot from a seeding density of 0.05 million cells/cm$^2$ is shown.
Figure 3B:
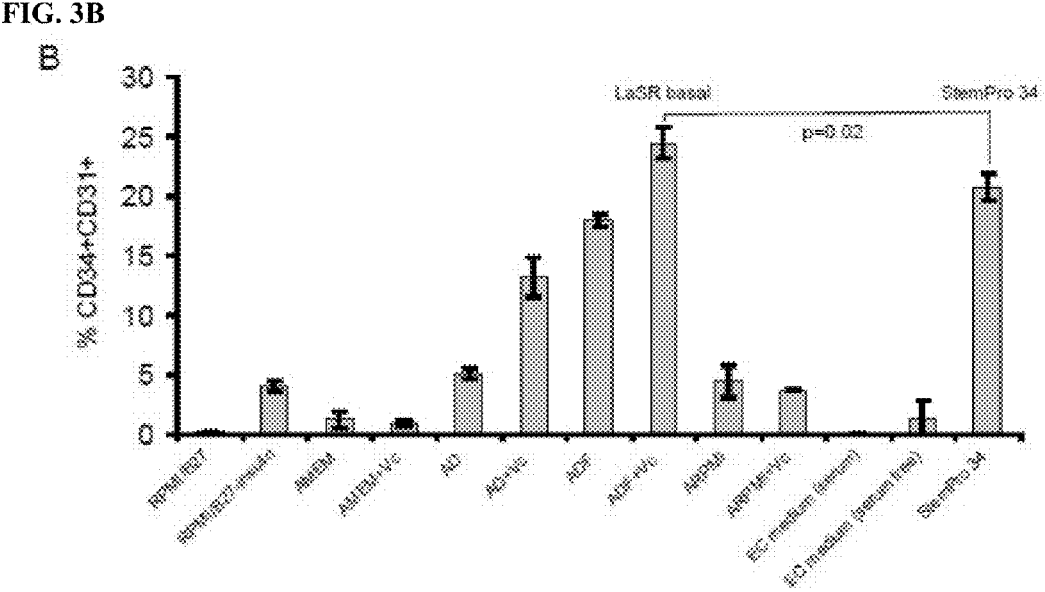

Differentiation Medium and Cell Density Dependence of Gsk3 Inhibitor-Induced Angioblast Differentiation We have shown that hPSCs can be differentiated to CD34+CD31+ angioblasts by two days (phase I) of culture in an optimized defined medium supplemented with Gsk3 inhibitors and another three days (phase II) in StemPro-34 medium. In order to streamline the differentiation pipeline, we tested whether a single basal medium could support angioblast differentiation (FIG. 3A). We examined 13 different media supplemented with CHIR99021 for two days (phase I) followed by three additional days in the same basal medium lacking exogenous growth factors or chemical inhibitors (phase II). We found that Advanced DMEM/F12 supplemented with ascorbic acid, which we termed "LaSR basal medium," was the most efficient for angioblast differentiation, resulting 25% CD34$^+$CD31$^+$ cells in 5 days (FIG. 3B). These results indicated the importance of basal medium composition in angioblast differentiation, with some media (e.g. RPMI/B27 and EC medium containing serum) not supporting differentiation to any detectable CD34$^+$CD31$^+$ cells (FIG. 3B).

Figure 3C:
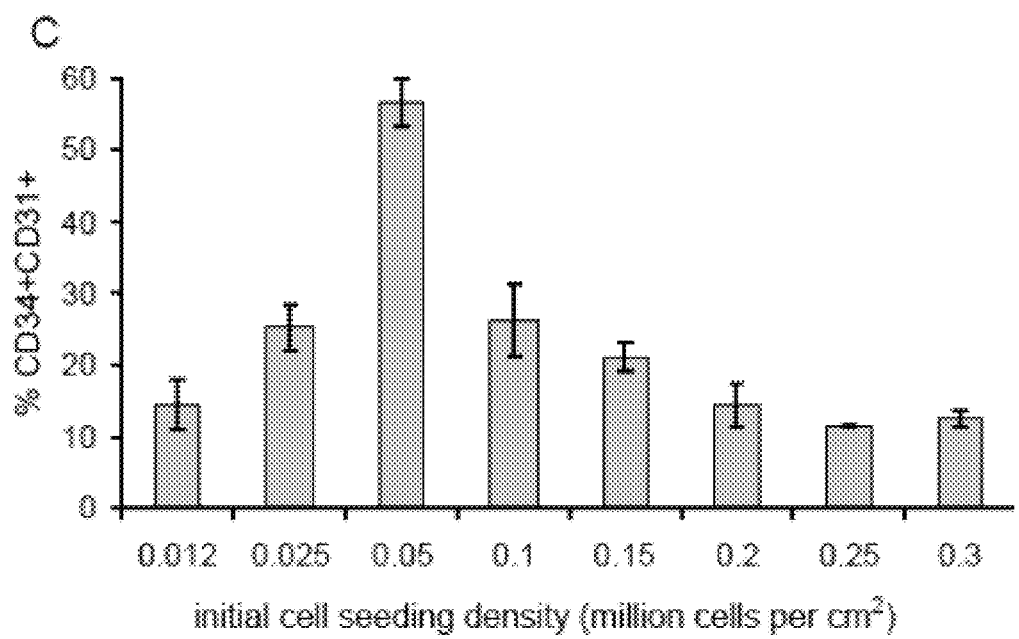
Figure 3D:
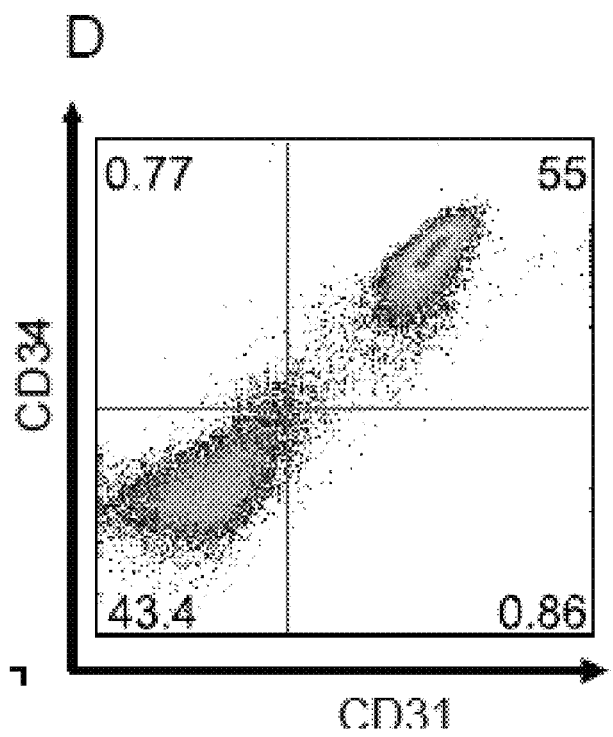

On the basis of the knowledge that initial cell density affects hPSC differentiation fates to lineages such as cardiomyocytes, epithelial progenitors, and pancreatic cells[39-42], we quantitatively assessed the effect of initial cell seeding density on angioblast differentiation efficiency. Singularized hPSCs were seeded at densities ranging from 12,000 to 300,000 cells per cm2, and then expanded in mTeSR1 for 3 days before transition to LaSR basal medium supplemented with CHIR99021 for 2 days and another 3 days in LaSR basal medium lacking CHIR99021. The optimal seeding density of 50,000 cells per cm2 at day −3, which resulted in 325,000 cells per cm2 at day 0, produced 55% CD34$^+$CD31$^+$ cells (FIGS. 3C and 3D).

Example 4 hPSC-Derived CD34$^+$CD31 Angioblasts are Multipotent

Figure 4A:
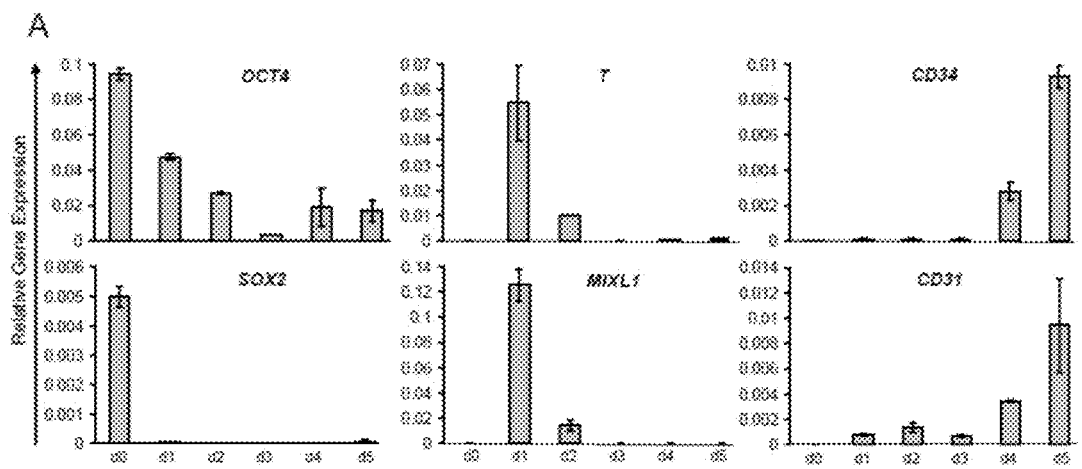
FIG. 4 Molecular analysis of angioblasts differentiated from hPSCs (A-C) 19-9-11 iPSCs were differentiated as illustrated in FIG. 3A using LaSR basal medium. At different time points, developmental gene or protein expression was assessed by (A) quantitative RT-PCR or (B) western blot. Error bars represent the s.e.m. of three independent experiments. (C) 5 days or 10 days post differentiation, immunostaining for CD34, CD31, and VE-cadherin were performed.
Figure 4B:
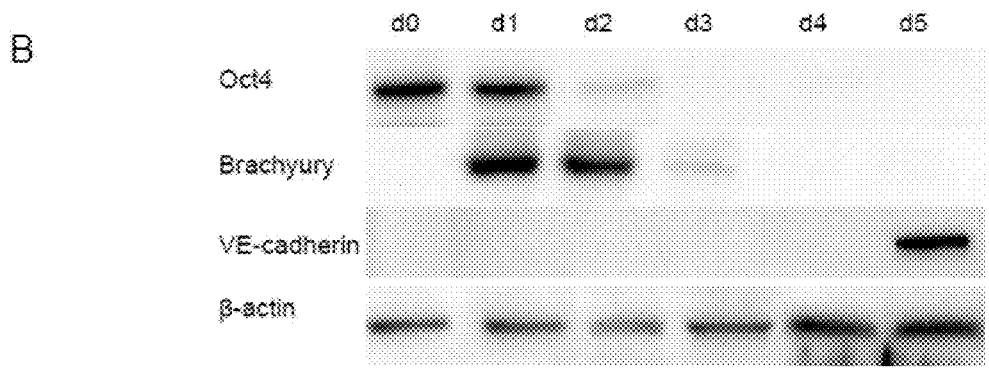
Figure 4C:
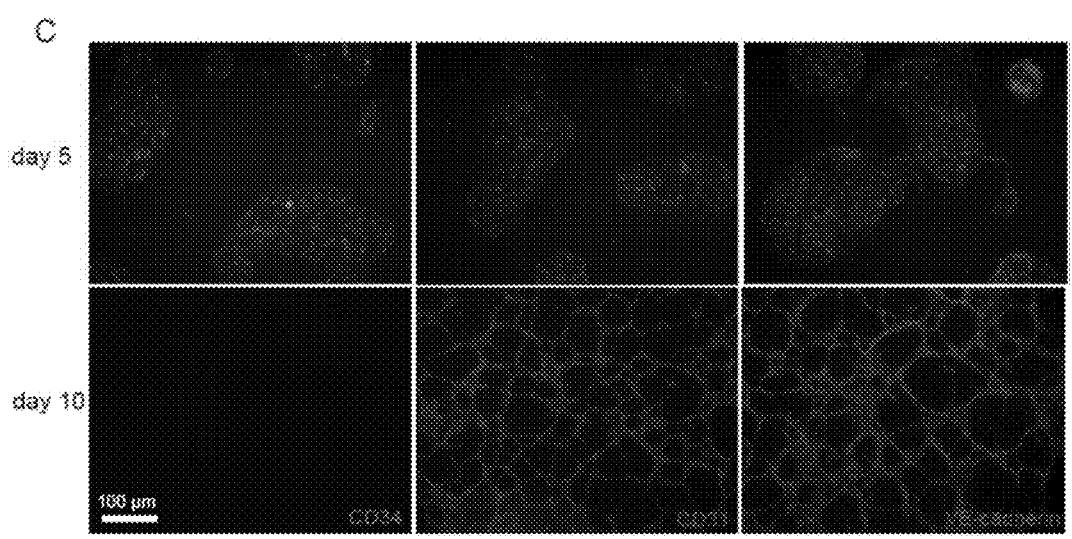
Figure 5A:
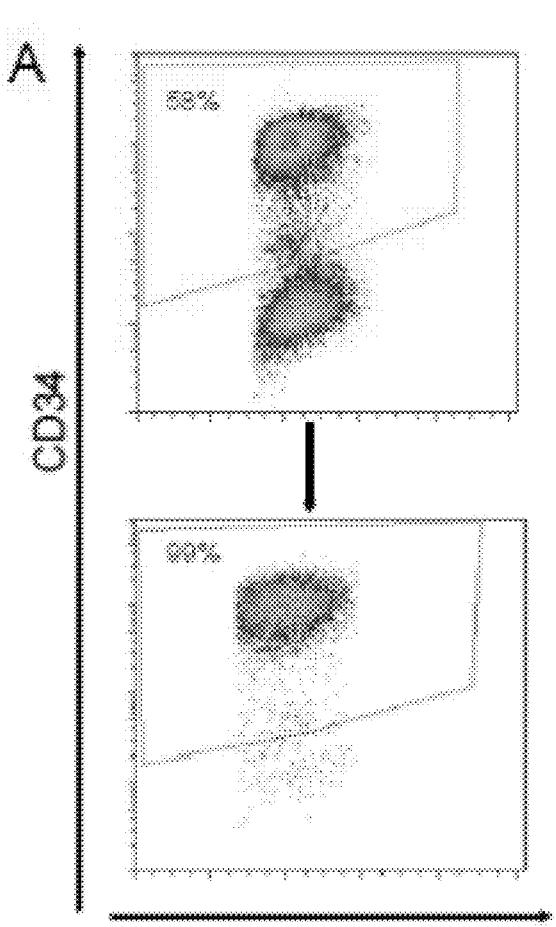
FIG. 5 CD34$^+$CD31$^+$ angioblasts are multipotent (A-E) 19-9-11 iPSCs were differentiated as illustrated in FIG. 3A using LaSR basal medium. (A) At day 5, CD34$^+$ cells were enriched with the EasySep™ Human CD34 Positive Selection Kit and purification quantified by flow cytometry for CD34 expression. (B-D) Sorted CD34$^+$ cells were cultured in (B) a combined medium, (C) smooth muscle medium, or (D) endothelial medium at a density of one cell per well of 48-well plate for another 10 days. Sample immunofluorescence images for smooth muscle and endothelial markers were shown. In (B), arrows point to SMMHC$^+$VE-cadherin- cells. (E) Day 5 CD34$^+$ angioblasts and day 15 endothelial cells were immunostained for developmental markers.
Figure 5B:
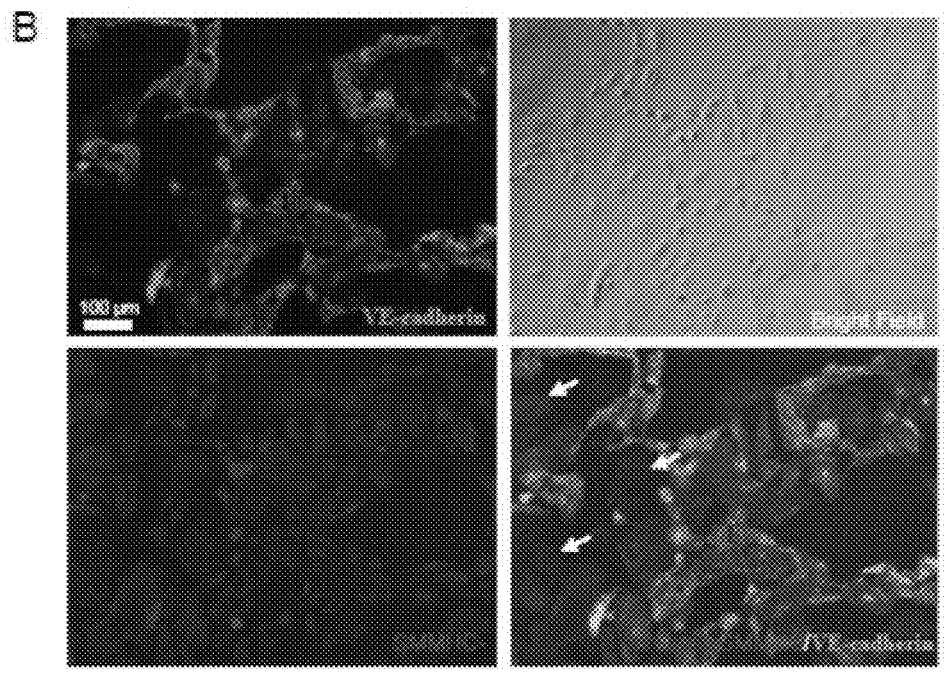
Figure 5E:
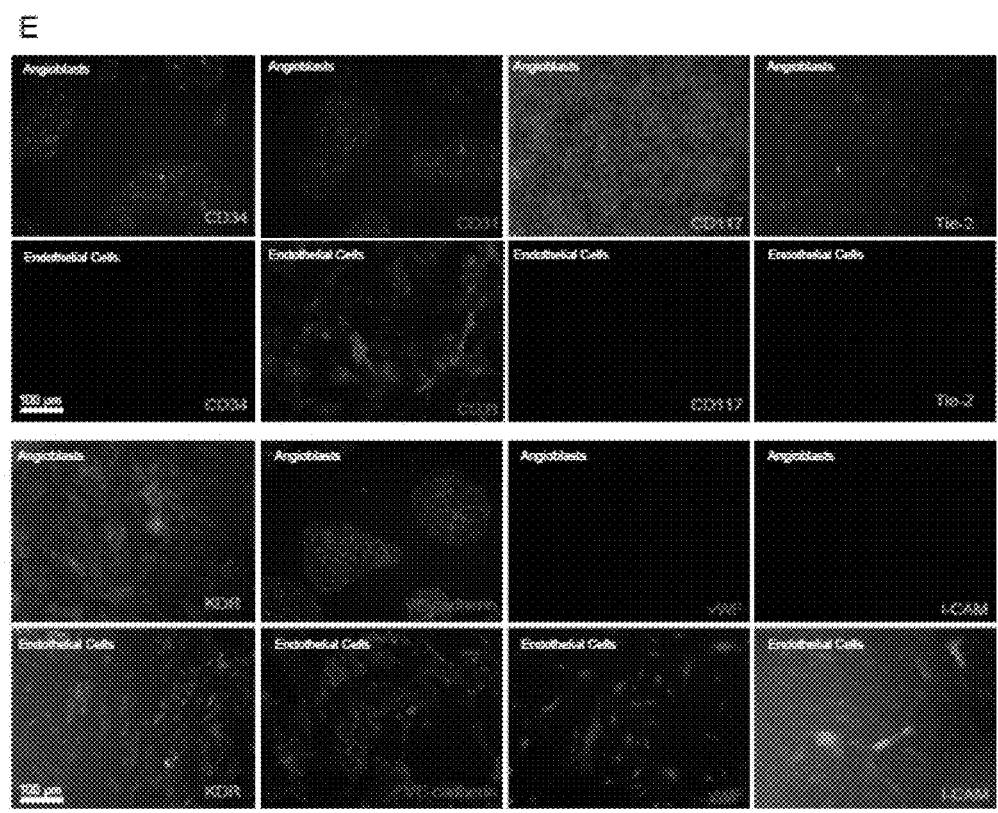

Molecular analysis of angioblast differentiation from hPSCs revealed dynamic changes in gene expression, with downregulation of the pluripotency markers SOX2 and OCT4, and induction of the primitive streak-like genes T[43] and MIXL1[44] in the first 24 hours after CH addition (FIG. 4A). Expression of the angioblast markers CD34 and CD31 was detected at day 4 and increased at day 5 (FIG. 4A). Western blot analysis of protein expression revealed decreasing Oct4 expression during the first two days of differentiation, and Brachyury induction on days 1 and 2 followed by downregulation on day 3. The endothelial marker VE-cadherin was only detected after 5 days of differentiation (FIG. 4B). Immunofluorescent analysis revealed the expression of CD34, CD31, and VE-cadherin on day 5 (FIG. 4C). Ten days after differentiation without passaging, however, the expression of CD34 diminished and the CD31$^+$ and VE-cadherin cells spontaneously formed networks of tube-like structures in the absence of exogenous VEGF treatment (FIG. 4C). To study the multipotent nature of the transient population of CD34$^+$ cells[45], we first enriched the day 5 differentiation culture to 99% purity of CD34$^+$ cells by magnetic-activated cell sorting (MACS) (FIG. 5A). The sorted CD34$^+$ putative angioblasts were plated on Matrigel™-coated 48-well plates at a density of one cell per well in a combined medium (50% smooth muscle and 50% endothelial medium). After 10 days of culture, the differentiation populations from 10 different single cell clones contained both VE-cadherin$^+$vWF$^+$ cells and Calponin$^+$SMMHC$^+$ (Smooth muscle myosin heavy chain) cells, including some cells expressing both endothelial and smooth muscle markers (FIG. 5B, FIG. 9A, B) thereby demonstrating that single CD34$^+$ angioblasts generated from hPSCs were multipotent. In addition, when the sorted CD34$^+$ clones were cultured in endothelial or smooth muscle medium rather than the mixed medium, they generated relatively pure populations of endothelial cells and smooth muscle cells, respectively (FIGS. 5C and D). The hPSC-derived angioblasts expressed c-kit (CD117), KDR (VEGFR2), Tie-2, CD31, CD34, CD144, but did not express vWF or I-CAM. However, the day 15 endothelial cells expressed CD31, CD144, vWF, I-CAM, and KDR, but did not express CD117, CD34, Tie-2 (FIG. 5E).

Example 5

Characterization of Endothelial Cells Derived from hPSCs

Figures 6A, 6B, 6C:
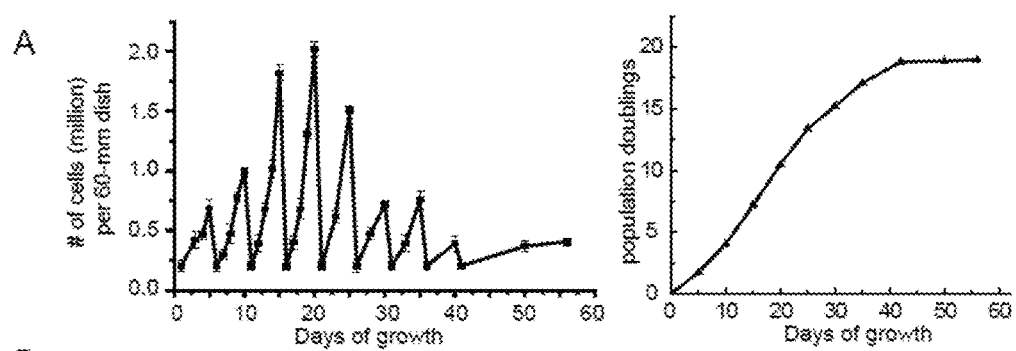
FIG. 6 Characterization of endothelial cells derived from hPSCs (A) 19-9-11 iPSCs were differentiated as illustrated in FIG. 3A using LaSR basal medium. At day 5, CD34$^+$ cells were enriched and cultured in endothelial medium on laminin-coated plates. At different time points, the cell numbers were counted. (B-D) the purified day 60 endothelial cells were immunostained with (B) VE-cadherin and CD31, and tested for (C) tube-forming ability upon VEGF treatment and the ability to (D) uptake acetylated low-density lipoprotein (AcLDL). (E) Flow cytometry analysis of surface protein expression of ICAM-1 of untreated cells or cells treated with 10 ng/mL TNF-α for 16 hours. Error bars represent the s.e.m. of three independent experiments. (F-G) Barrier phenotype of the hPSC-derived endothelial cells. Endothelial cells were differentiated as illustrated in FIG. 3A using LaSR basal medium and then CD34$^+$ cells were enriched by MACS and cultured on laminin in endothelial cell medium. After 10 days in culture, the endothelial cells were seeded on collagen/fibronectin coated transwell filters and maintained in endothelial serum free medium. Barrier function was assessed by measuring transendothelial electrical resistance (TEER) 48 hours after seeding. Next, cells were treated with endothelial SFM containing 100 ng/mL VEGF or 10 µM oME. (F) Transendothelial electrical resistance (TEER) was measured as a function of time, and normalized to the initial TEER value (36.7±4.3 Ωcm$^2$. (G) TEER and fluorescent dextran permeability were measured 24 hours after plating. Error bars represent the s.e.m. of three biological samples. ** p<0.005, VEGF (or oME) versus control; t test.

To study the intrinsic properties of endothelial cells differentiated from hPSCs by Gsk3 inhibition and culture in LaSR medium, we cultivated the purified CD34$^+$ cells in endothelial medium on laminin-coated plates and found that the resulting CD34$^+$CD31$^+$vWF$^+$CD144$^+$endothelial cells were capable of approximately 20 population doublings over 2 months, generating more than 1 million cells from a single endothelial cell (FIG. 6A). After two months in culture, the cells still expressed CD31 and VE-cadherin (FIG. 6B). Furthermore, upon treatment with exogenous VEGF, the CD144 cells formed vascular tubes in Matrigel™ matrix (FIG. 6C) and were capable of acetylated low-density lipoprotein (AcLDL) uptake, indicative of endothelial function (FIG. 6D). The endothelium also responds to inflammatory mediators, such as TNFα, by up-regulating adhesion molecules including ICAM-1, which has been implicated in the capture of circulating leukocytes. While unstimulated endothelial cells expressed low levels of ICAM1, TNFα-treatment greatly increased the expression of ICAM1 in the hPSC-derived endothelial cells (FIG. 6E).

To characterize the barrier phenotype of the hPSC-derived endothelial cells, we measured the transendothelial electrical resistance (TEER) and transport of fluorescent 40 kD dextran across a monolayer of differentiated endothelial cells. VEGF treatment induced a sustained decrease in TEER and an increase in dextran permeability. However, treatment of endothelial cells with the cAMP analog, 8-pCPT-2'O-Me-cAMP (o-Me) decreased dextran permeability and increased TEER (FIGS. 6F and 6G).

Prior reports of differentiating hPSCs to endothelial cells required the addition of expensive growth factors and/or undefined serum to direct endothelial development and these methods generated heterogeneous cell mixtures typically containing less than 10% endothelial cells[42-48]. Here we show that small-molecule activation of canonical Wnt signaling via Gsk3 inhibition, in the absence of exogenous growth factors, is sufficient to generate high yields of CD34$^+$CD31$^+$ bipotent angioblasts from hPSCs. Prior to this study, angioblasts have not been isolated from hPSCs under defined conditions and the mechanisms by which developmental signaling pathways regulate angioblast commitment remained largely unknown[46]. With a doxycycline-inducible shRNA knockdown of the Wnt pathway modulator β-catenin, we identified that β-catenin is required for CD34$^+$CD31$^+$ angioblast generation from hPSCs following Gsk3 inhibition. Furthermore, while previous reports required more than 10 days to generate CD34$^+$CD31$^+$ cells[42-48], this small molecule differentiation approach accelerates developmental timing and converts hPSCs to greater than 50% CD34$^+$CD31$^+$ cells in 5 days. By a single magnetic affinity separation step, the populations can be enriched more than 99% CD34$^+$CD31$^+$ cells.

Gsk3 inhibition has been shown to be a potent inducer of mesendoderm lineage commitment in hPSCs[47]. The Wnt pathway exhibits crosstalk with a variety of other developmental signaling networks, including TGFβ superfamily[48], FGF[49], Notch[50], Hippo[51], and retinoic acid signaling[52]. The necessity of β-catenin in generating CD34+CD31+ cells indicates a direct role of canonical Wnt signaling in angioblast differentiation, while the diminished yield of CD34+CD31+ cells in the presence of an FGF2 inhibitor suggests that this pathway, and perhaps other endogenous pathways, also mediates angioblast differentiation. Thus, canonical Wnt signaling is not the only pathway required for angioblast specification, but it may act as a master regulator to orchestrate signaling that leads to angioblast differentiation.

We have previously reported a method to differentiate hPSCs to a relatively pure population of cardiomyocytes by dynamic modulation of canonical Wnt signaling using small-molecule Gsk3 inhibitors and Porcupine inhibitors in a RPMI basal medium[35,39]. This protocol uses Wnt pathway activation to direct mesendoderm differentiation, followed by Wnt pathway inhibition to specify cardiac mesoderm and cardiomyocyte fates. While the small-molecule cardiomyocyte and angioblast differentiation protocols result in optimal cell yields in distinct defined basal media, both progress through mesodermal progenitors via Gsk3 inhibition. These mesodermal progenitors can be directed to spontaneously-contracting cardiomyocytes via Wnt inhibition, while permitting endogenous canonical Wnt signaling yields a population enriched in angioblasts. Together, these results demonstrate the concept of chemically guiding differentiation to distinct cell types via different patterns of modulation of master regulators of cell fates. This paradigm may represent a promising general approach to efficiently produce cells and tissues from stem cell sources in a defined manner.

Interestingly, the Wnt pathway-induced angioblast differentiation protocol primarily generates CD34 and CD31 double positive cells, as opposed to other methods using BMP4 which produce a mixture of CD34+CD31-, CD34+CD31+, CD34-CD31+ cells[30,32]. The CD34+CD31+ angioblasts may be more amenable to large scale expansion. Furthermore, these angioblasts can be further directed to endothelial cells or smooth muscle cells by culture in the appropriate inductive media. Purified CD31+VE-cadherin+vWF+CD34-endothelial cells were expanded for 20 doublings over 2 months and maintained expression of endothelial cell markers (CD31+VE-cadherin+CD34-). These cells exhibited uptake of acetylated low-density lipoprotein and formed tube-like structures when cultured on Matrigel™. These endothelial cells also responded to TNFα treatment by increasing ICAM-1 expression and maintained a dynamic barrier, responding to VEGF and cAMP analog by increasing or decreasing dextran permeability, respectively. Our findings are the first demonstration of achieving efficient and reproducible angioblast and endothelial differentiation of hPSCs by Gsk3 inhibition in the absence of exogenous growth factor stimulation.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A method for generating a cell population comprising endothelial cells from human pluripotent stem cells, comprising the steps of:
   (i) contacting cultured human pluripotent stem cells with an activator of Wnt/β-catenin signaling for a period of about two days in a cell culture medium suitable for maintenance of human endothelial cells, but substantially free of exogenous growth factors; and
   (ii) obtaining a cell population comprising endothelial cells by culturing the contacted cells in the absence of the activator, for at least about three days to about ten days, in a cell culture medium suitable for maintenance of human endothelial cells but substantially free of exogenous growth factors.

2. The method of claim 1, wherein the cultured human pluripotent stem cells are cultured at a density of about 250,000 cells/cm² to about 400,000 cells/cm² at the beginning of the contacting step.

3. The method of claim 1, wherein the cell culture medium is selected from the group consisting of Advanced™ DMEM, VcG-Advanced™ DMEM, LaSR medium, Advanced™ DMEM-F12; VcG-Advanced™ DMEM-F12, StemPro® 34 medium, Advanced™ RPMI, and VcG-Advanced™ RPMI.

4. The method of claim 1, wherein the cell culture medium substantially free of exogenous growth factors is LaSR medium.

5. The method of claim 1, wherein the activator of Wnt/β-catenin signaling is a Gsk3 inhibitor.

6. The method of claim 5, wherein the Gsk3 inhibitor is selected from the group consisting of CHIR 99021, CHIR 98014, BIO-acetoxime, BIO, LiCl, SB 216763, SB 415286, AR A014418, 1-Azakenpaullone, and Bis-7-indolylmaleimide.

7. The method of claim 1, wherein the Gsk3 inhibitor is CHIR 99021, CHIR 98014, or BIO-acetoxime.

8. The method of claim 7, wherein the Gsk3 inhibitor is CHIR 99021 or CHIR 98014 at a concentration of at least about 4 µM to about 10 µM in the medium.

9. The method of claim 1, wherein the obtained cell population comprises at least 50% endothelial cells.

10. The method of claim 1, wherein in step (ii) the contacted cells are cultured in the absence of the activator for about ten days.

11. A kit for differentiating human pluripotent stem cells into endothelial cells, the kit comprising:
(i) a Gsk3 inhibitor;
(ii) a culture medium substantially free of exogenous growth factors and suitable for differentiation of human pluripotent stem cells into endothelial cells; and
(iii) instructions describing a method for differentiating human pluripotent stem cells into endothelial cells, the method employing the Gsk3 inhibitor and the culture medium.

12. The kit of claim 11, wherein the culture medium is selected from the group consisting of Advanced™ DMEM, VcG-Advanced™ DMEM, LaSR medium, Advanced™ DMEM-F12; VcG-Advanced™ DMEM-F12, StemPro® 34 medium, Advanced™ RPMI, and VcG-Advanced™ RPMI.

13. A method for generating a cell population comprising $CD31^+$ cells from human pluripotent stem cells, comprising the steps of:
(i) contacting cultured human pluripotent stem cells with an activator of Wnt/β-catenin signaling for a period of about two days in a cell culture medium suitable for maintenance of human endothelial cells, but substantially free of exogenous growth factors; and
(ii) obtaining a cell population comprising $CD31^-$ cells by culturing the contacted cells in the absence of the activator, for about three days to about ten days, in a cell culture medium suitable for maintenance of human endothelial cells but substantially free of exogenous growth factors.

14. The method of claim 13, wherein the cell population from step (ii) is cultured for about ten days in the cell culture medium suitable for maintenance of human endothelial cells.

15. The method of claim 13, further comprising subjecting the cell population of step (ii) to selection for $CD34^+$ cells to obtain a cell population enriched for angioblasts.

* * * * *

SEQUENCE LISTING

<160> NUMBER OF SEQ ID NOS: 18

<210> SEQ ID NO 1
<211> LENGTH: 19
<212> TYPE: DNA
<213> ORGANISM: Homo sapiens

<400> SEQUENCE: 1
cagtgcccga aacccacac                                                19

<210> SEQ ID NO 2
<211> LENGTH: 20
<212> TYPE: DNA
<213> ORGANISM: Homo sapiens

<400> SEQUENCE: 2
ggagacccag cagcctcaaa                                               20

<210> SEQ ID NO 3
<211> LENGTH: 20
<212> TYPE: DNA
<213> ORGANISM: Homo sapiens

<400> SEQUENCE: 3
caagatgcac aactcggaga                                               20

<210> SEQ ID NO 4
<211> LENGTH: 20
<212> TYPE: DNA
<213> ORGANISM: Homo sapiens

<400> SEQUENCE: 4
gttcatgtgc gcgtaactgt                                               20

```
<210> SEQ ID NO 5
<211> LENGTH: 20
<212> TYPE: DNA
<213> ORGANISM: Homo sapiens

<400> SEQUENCE: 5
cagagtggga aatccttcca                                               20

<210> SEQ ID NO 6
<211> LENGTH: 20
<212> TYPE: DNA
<213> ORGANISM: Homo sapiens

<400> SEQUENCE: 6
tgagtccagc tttgaaccaa                                               20

<210> SEQ ID NO 7
<211> LENGTH: 20
<212> TYPE: DNA
<213> ORGANISM: Homo sapiens

<400> SEQUENCE: 7 gctgacccttt ctgctctgtt                                              20

<210> SEQ ID NO 8
<211> LENGTH: 20
<212> TYPE: DNA
<213> ORGANISM: Homo sapiens

<400> SEQUENCE: 8
tgagaggtgg tgctgacatc                                               20

<210> SEQ ID NO 9
<211> LENGTH: 22
<212> TYPE: DNA
<213> ORGANISM: Homo sapiens

<400> SEQUENCE: 9
cctaagtgac atcaaggcag aa                                            22

<210> SEQ ID NO 10
<211> LENGTH: 19
<212> TYPE: DNA
<213> ORGANISM: Homo sapiens

<400> SEQUENCE: 10
gcaaggagca gggagcata                                                19

<210> SEQ ID NO 11
<211> LENGTH: 21
<212> TYPE: DNA
<213> ORGANISM: Homo sapiens

<400> SEQUENCE: 11
cctgaaccct aaggccaacc g                                             21

<210> SEQ ID NO 12
<211> LENGTH: 21
<212> TYPE: DNA
<213> ORGANISM: Homo sapiens

<400> SEQUENCE: 12
gctcatagct cttctccagg g                                             21
```

```
<210> SEQ ID NO 13
<211> LENGTH: 20
<212> TYPE: DNA
<213> ORGANISM: Homo sapiens

<400> SEQUENCE: 13
gtggacctga cctgccgtct                                               20

<210> SEQ ID NO 14
<211> LENGTH: 20
<212> TYPE: DNA
<213> ORGANISM: Homo sapiens

<400> SEQUENCE: 14
ggaggagtgg gtgtcgctgt                                               20

<210> SEQ ID NO 15
<211> LENGTH: 20
<212> TYPE: DNA
<213> ORGANISM: Homo sapiens

<400> SEQUENCE: 15
aagaaggaaa tgcagcctca                                               20

<210> SEQ ID NO 16
<211> LENGTH: 20
<212> TYPE: DNA
<213> ORGANISM: Homo sapiens

<400> SEQUENCE: 16
tactgcaggt gtgagcaagg                                               20

<210> SEQ ID NO 17
<211> LENGTH: 20
<212> TYPE: DNA
<213> ORGANISM: Homo sapiens

<400> SEQUENCE: 17
cccactaatg tccagcgttt                                               20

<210> SEQ ID NO 18
<211> LENGTH: 20
<212> TYPE: DNA
<213> ORGANISM: Homo sapiens

<400> SEQUENCE: 18
aacgcatgat agcgtgtctg                                               20
```